United States Patent
Yoneyama et al.

(10) Patent No.: US 11,594,051 B2
(45) Date of Patent: Feb. 28, 2023

(54) MICROSCOPE SYSTEM AND PROJECTION UNIT

(71) Applicant: Evident Corporation, Nagano (JP)

(72) Inventors: Takashi Yoneyama, Tokyo (JP); Akifumi Kabeya, Tokyo (JP); Yosuke Tani, Tokyo (JP); Tatsuo Nakata, Tokyo (JP); Masayoshi Karasawa, Tokyo (JP)

(73) Assignee: Evident Corporation, Nagano (JP)

( * ) Notice: Subject to any disclaimer, the term of this patent is extended or adjusted under 35 U.S.C. 154(b) by 0 days.

(21) Appl. No.: 17/196,921

(22) Filed: Mar. 9, 2021

(65) Prior Publication Data

US 2021/0192181 A1    Jun. 24, 2021

Related U.S. Application Data

(63) Continuation of application No. PCT/JP2018/047499, filed on Dec. 25, 2018.

(30) Foreign Application Priority Data

Sep. 28, 2018  (JP) .............................. JP2018-183763

(51) Int. Cl.
*G06V 20/69* (2022.01)
*G06T 7/90* (2017.01)
(Continued)

(52) U.S. Cl.
CPC ......... *G06V 20/698* (2022.01); *G06K 9/6277* (2013.01); *G06T 7/90* (2017.01);
(Continued)

(58) Field of Classification Search
CPC .. G06V 20/698; G06V 2201/03; G06V 10/40; G06V 20/69; G06K 9/6277;
(Continued)

(56) References Cited

U.S. PATENT DOCUMENTS

| | | |
|---|---|---|
| 4,672,559 A | 6/1987 | Jansson et al. |
| 6,239,909 B1 | 5/2001 | Hayashi et al. |
| | (Continued) | |

FOREIGN PATENT DOCUMENTS

| | | |
|---|---|---|
| JP | S61156214 A | 7/1986 |
| JP | H0580255 A | 4/1993 |
| | (Continued) | |

OTHER PUBLICATIONS

Microscope World, Infinity Corrected Optics, Apr. 2015, www.microscopeworld.co/t-infinity_corrected_optics.aspx (Year: 2015).*

(Continued)

*Primary Examiner* — Marnie A Matt
(74) *Attorney, Agent, or Firm* — Holtz, Holtz & Volek PC

(57) ABSTRACT

A microscope system includes an eyepiece, an objective, a tube lens that is disposed between the eyepiece and the objective, a projection apparatus that projects a projection image onto an image plane on which an optical image is formed by the tube lens, and a processor that performs processes. The processes include performing for digital image data of the sample at least one analysis process selected from a plurality of analysis processes, and generating projection image data representing the projection image on the basis of the analysis result and the at least one analysis process. The projection image data indicates the analysis result in a display format including an image color corresponding to the at least one analysis process. The generating the projection image data includes determining a color for the projection image in accordance with the at least one analysis process selected from the plurality of analysis processes.

16 Claims, 22 Drawing Sheets

(51) Int. Cl.
*G16H 50/20* (2018.01)
*G16H 30/40* (2018.01)
*G06K 9/62* (2022.01)
*H04N 9/31* (2006.01)

(52) U.S. Cl.
CPC .............. *G16H 30/40* (2018.01); *G16H 50/20* (2018.01); *H04N 9/317* (2013.01); *G06T 2207/10024* (2013.01); *G06T 2207/10056* (2013.01); *G06V 2201/03* (2022.01)

(58) Field of Classification Search
CPC ............. G06T 7/90; G06T 2207/10024; G06T 2207/10056; G06T 7/0014; G06T 7/0016; G06T 2200/24; G06T 2207/20081; G06T 2207/20084; G06T 2207/30024; G06T 7/12; G16H 30/40; G16H 50/20; H04N 9/317; G02B 21/00; G02B 21/36
USPC .......................................................... 348/79
See application file for complete search history.

(56) References Cited

U.S. PATENT DOCUMENTS

| | | | |
|---|---|---|---|
| 6,304,372 | B1 | 10/2001 | Spink |
| 6,483,948 | B1 | 11/2002 | Spink et al. |
| 7,428,324 | B2 | 9/2008 | Crandall et al. |
| 9,971,966 | B2 | 5/2018 | Nelson et al. |
| 10,078,205 | B2 | 9/2018 | Hauger et al. |
| 2001/0055062 | A1 | 12/2001 | Shioda et al. |
| 2003/0123717 | A1 | 7/2003 | Bacus et al. |
| 2006/0228107 | A1 | 10/2006 | Takamatsu et al. |
| 2007/0076232 | A1 | 4/2007 | Olschewski et al. |
| 2007/0147673 | A1 | 6/2007 | Crandall |
| 2012/0013728 | A1 | 1/2012 | Matsuo |
| 2013/0044185 | A1 | 2/2013 | Krishnaswamy et al. |
| 2013/0070077 | A1* | 3/2013 | Winkelman ............. H04N 7/18 348/79 |
| 2013/0188033 | A1 | 7/2013 | Oda et al. |
| 2014/0072195 | A1* | 3/2014 | Zhang .................. G06V 20/698 382/129 |
| 2014/0314299 | A1 | 10/2014 | Santamaria-Pang et al. |
| 2014/0333997 | A1 | 11/2014 | Oda |
| 2014/0340426 | A1 | 11/2014 | Furuhata |
| 2015/0049936 | A1* | 2/2015 | Tsunomori ........... G06V 20/695 382/133 |
| 2015/0130920 | A1 | 5/2015 | Zou et al. |
| 2015/0209116 | A1 | 7/2015 | Wirth et al. |
| 2015/0370059 | A1 | 12/2015 | Hoegele et al. |
| 2016/0062098 | A1 | 3/2016 | Brown |
| 2016/0103308 | A1 | 4/2016 | Furuya |
| 2016/0116724 | A1 | 4/2016 | Abe |
| 2016/0166194 | A1* | 6/2016 | Gareau .............. A61B 5/14551 600/328 |
| 2016/0170194 | A1 | 6/2016 | Mueller et al. |
| 2016/0206198 | A1 | 7/2016 | Weber |
| 2016/0266369 | A1 | 9/2016 | Hauger et al. |
| 2016/0357003 | A1 | 12/2016 | Hauger et al. |
| 2017/0262984 | A1* | 9/2017 | Barnes ...................... G06T 7/11 |
| 2018/0267287 | A1 | 9/2018 | Regensburger et al. |
| 2018/0275388 | A1 | 9/2018 | Zou et al. |
| 2018/0307034 | A1 | 10/2018 | Saur et al. |
| 2018/0348496 | A1 | 12/2018 | Brown |
| 2019/0076020 | A1 | 3/2019 | Steffen et al. |
| 2019/0195777 | A1 | 6/2019 | Matsubara |
| 2020/0211233 | A1* | 7/2020 | Siegel .................. G02B 21/361 |
| 2021/0191101 | A1 | 6/2021 | Kabeya et al. |
| 2021/0192179 | A1 | 6/2021 | Nakata et al. |
| 2021/0192181 | A1 | 6/2021 | Yoneyama et al. |
| 2021/0215923 | A1 | 7/2021 | Nakata et al. |
| 2021/0319208 | A1 | 10/2021 | Ohara et al. |

FOREIGN PATENT DOCUMENTS

| | | |
|---|---|---|
| JP | H07253548 A | 10/1995 |
| JP | H08029694 A | 2/1996 |
| JP | H11242189 A | 9/1999 |
| JP | 2000292422 A | 10/2000 |
| JP | 2001519944 A | 10/2001 |
| JP | 2003116874 A | 4/2003 |
| JP | 2005351916 A | 12/2005 |
| JP | 2006071430 A | 3/2006 |
| JP | 2006292999 A | 10/2006 |
| JP | 2006297060 A | 11/2006 |
| JP | 2008090072 A | 4/2008 |
| JP | 2012019748 A | 2/2012 |
| JP | 2013054083 A | 3/2013 |
| JP | 2013072997 A | 4/2013 |
| JP | 2014063041 A | 4/2014 |
| JP | 2014222321 A | 11/2014 |
| JP | 2015141420 A | 8/2015 |
| JP | 2016517115 A | 6/2016 |
| JP | 2016133668 A | 7/2016 |
| JP | 2016526185 A | 9/2016 |
| JP | 2017161262 A | 9/2017 |
| JP | 2018010021 A | 1/2018 |
| JP | 2018054425 A | 4/2018 |
| JP | 2018066908 A | 4/2018 |
| JP | 2018128532 A | 8/2018 |
| WO | 2012117647 A1 | 9/2012 |
| WO | 2013094434 A1 | 6/2013 |
| WO | 2016130424 A1 | 8/2016 |
| WO | 2018042413 A1 | 3/2018 |

OTHER PUBLICATIONS

Office Action (Non-Final Rejection) dated Apr. 11, 2022, issued in related U.S. Appl. No. 17/196,634.
Japanese Office Action dated Apr. 5, 2022 (and English translation thereof) issued in Japanese Application No. 2020-547904.
Japanese Office Action (and English language translation thereof) dated Apr. 19, 2022, issued in Japanese Application No. 2020-547901 (which is a counterpart of related U.S. Appl. No. 17/196,634).
Japanese Office Action (and English language translation thereof) dated Apr. 19, 2022, issued in Japanese Application No. 2020-547903 (which is a counterpart of related U.S. Appl. No. 17/195,916).
Japanese Office Action (and English language translation thereof) dated Apr. 26, 2022, issued in Japanese Application No. 2020-547902 (which is a counterpart of related U.S. Appl. No. 17/196,705).
International Search Report (ISR) (and English translation thereof) dated Mar. 26, 2019 issued in International Application No. PCT/JP2018/047492.
International Search Report (ISR) (and English translation thereof) dated Mar. 26, 2019 issued in International Application No. PCT/JP2018/047494.
International Search Report (ISR) (and English translation thereof) dated Mar. 26, 2019 issued in International Application No. PCT/JP2018/047498.
U.S. Appl. No. 17/195,916, First Named Inventor: Tatsuo Nakata; Title: "Microscope System, Projection Unit, and Image Projection Method"; Filed: Mar. 9, 2021.
U.S. Appl. No. 17/196,634, First Named Inventor: Akifumi Kabeya; Title: "Microscope System, Projection Unit, and Image Projection Method"; Filed: Mar. 9, 2021.
U.S. Appl. No. 17/196,705, First Named Inventor: Tatsuo Nakata; Title: "Microscope System"; Filed Mar. 9, 2021.
U.S. Appl. No. 17/195,916, filed Mar. 9, 2021.
U.S. Appl. No. 17/196,705, filed Mar. 9, 2021; and.
U.S. Appl. No. 17/196,634, filed Mar. 9, 2021.
International Search Report (ISR) (and English translation thereof) dated Mar. 12, 2019 issued in International Application No. PCT/JP2018/047499.
Chinese Office Action (and English language translation thereof) dated May 12, 2022, issued in Chinese Application No. 201880097755.4 (which is a counterpart of related U.S. Appl. No. 17/196,634).

(56) References Cited

OTHER PUBLICATIONS

Chinese Office Action (and English language translation thereof) dated Jul. 5, 2022, issued in counterpart Chinese Application No. 201880097759.2.
Japanese Office Action (and English language translation thereof) dated Nov. 1, 2022, issued in counterpart Japanese Application No. 2020-547904.

* cited by examiner

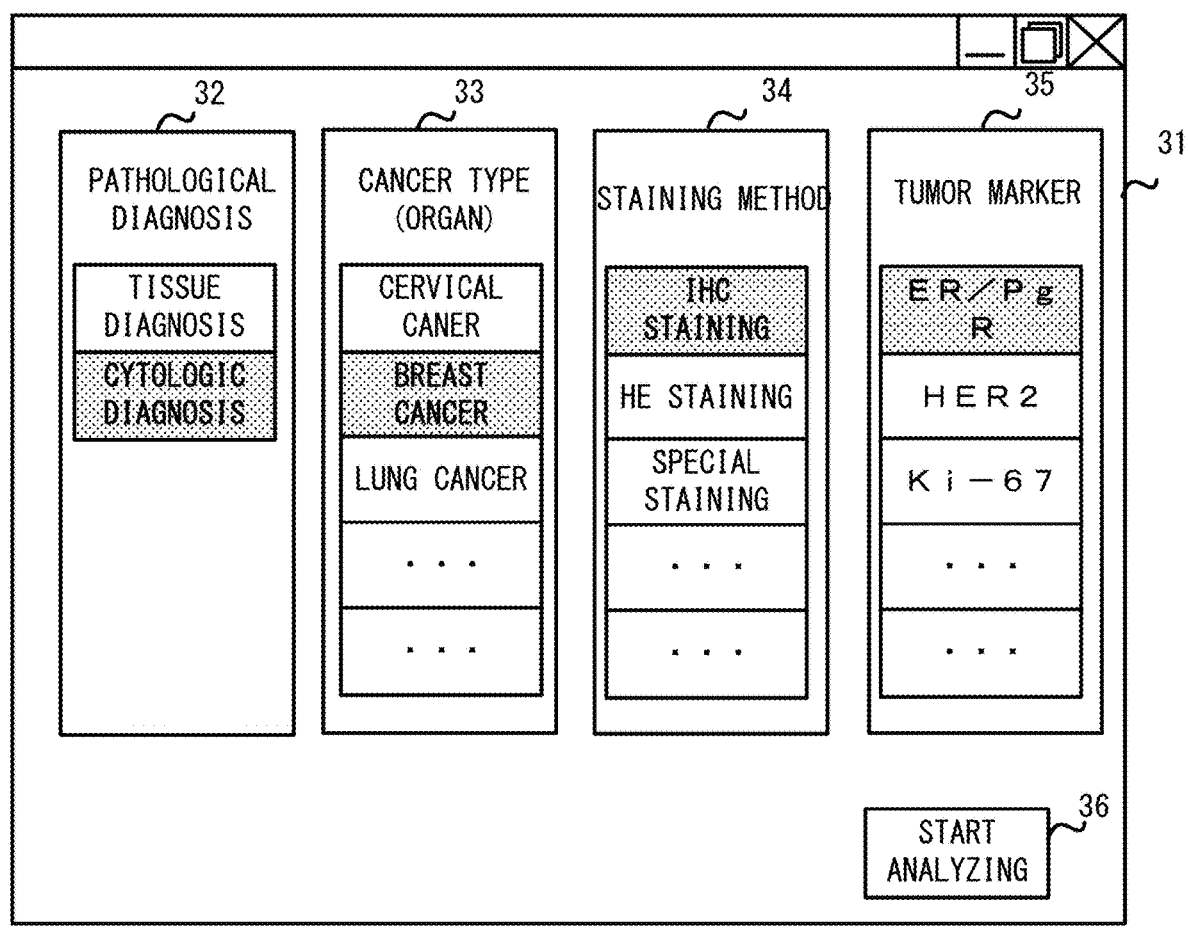
F I G. 4

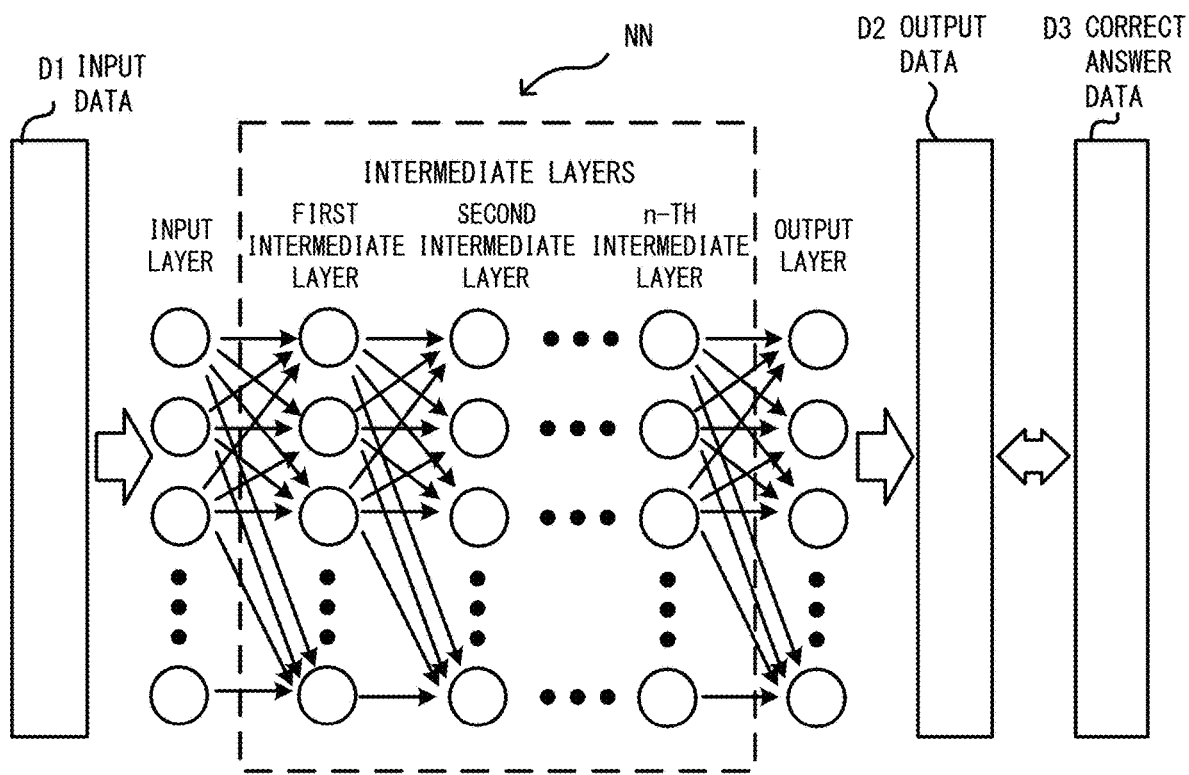
F I G. 1 1

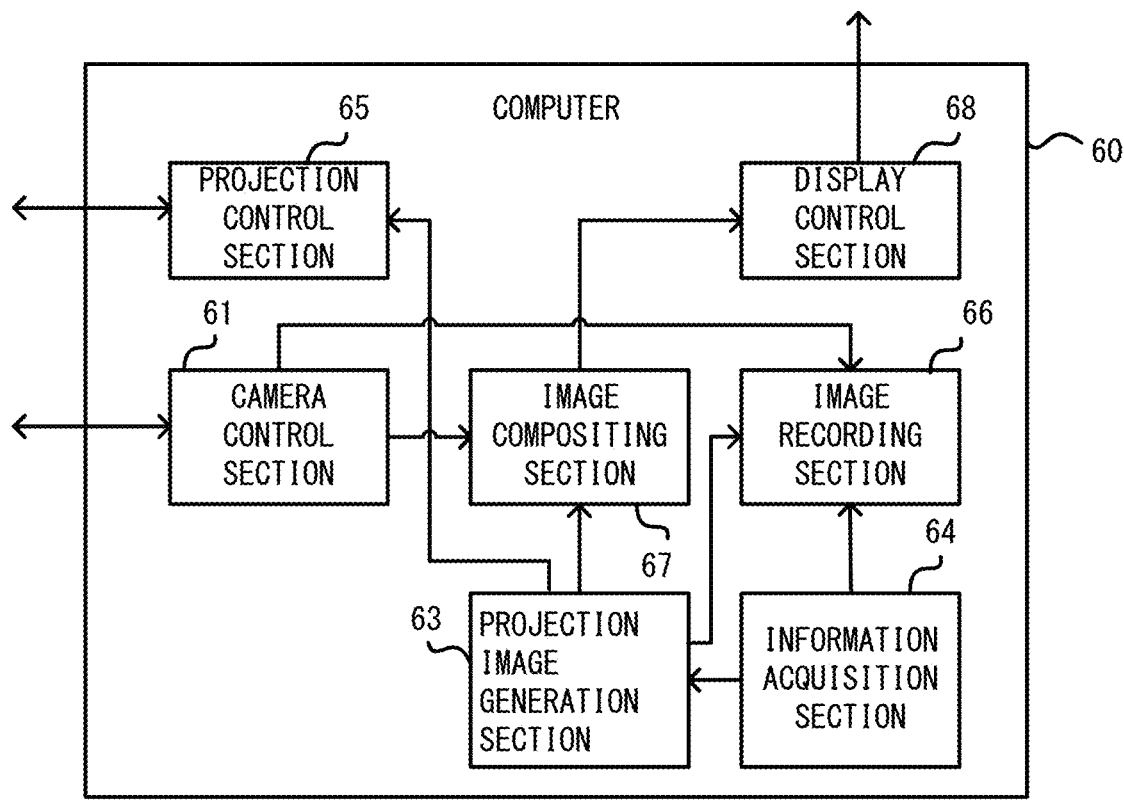
F I G. 1 3

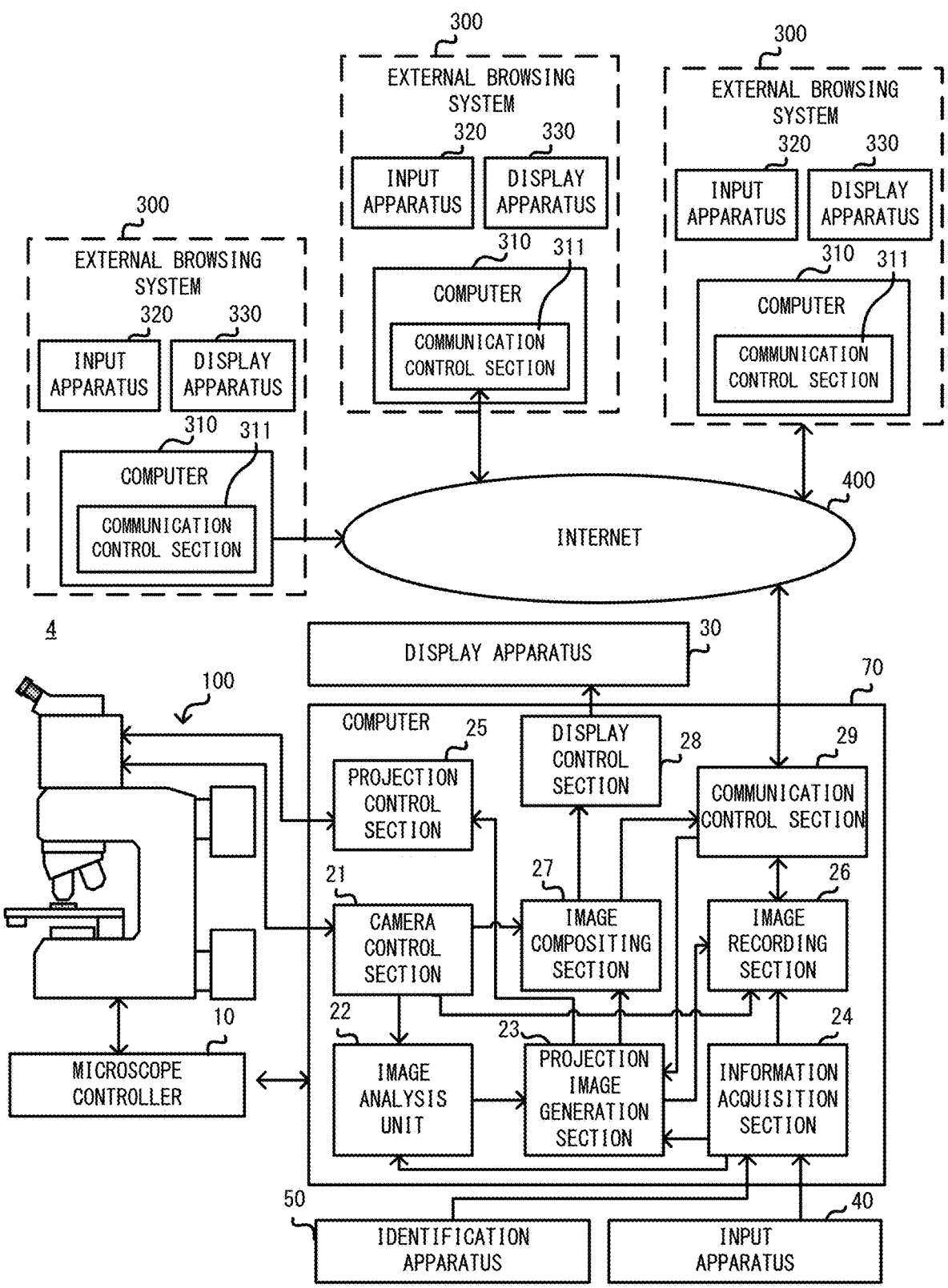
F I G. 19

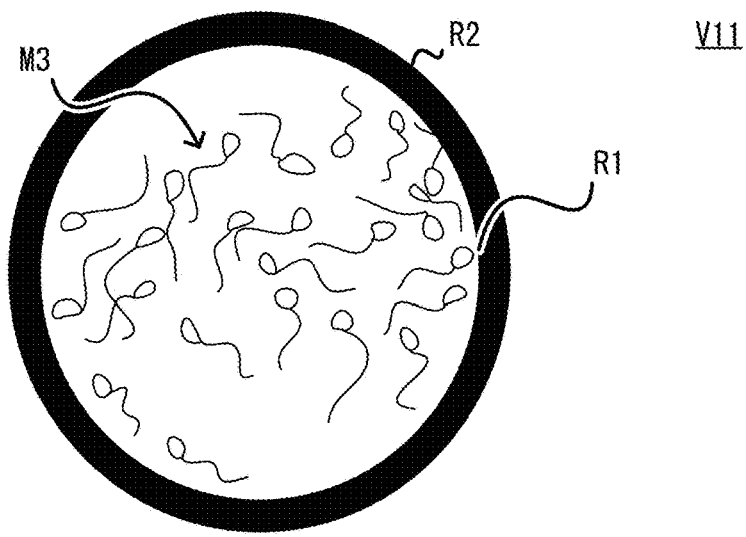
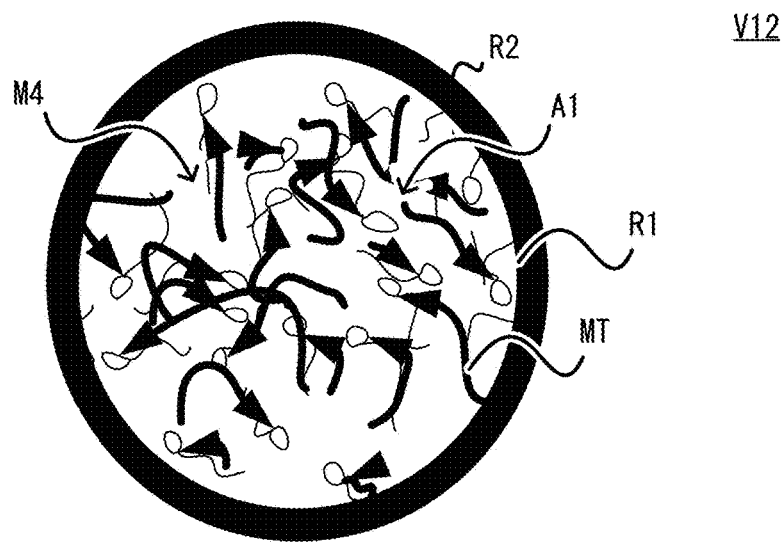
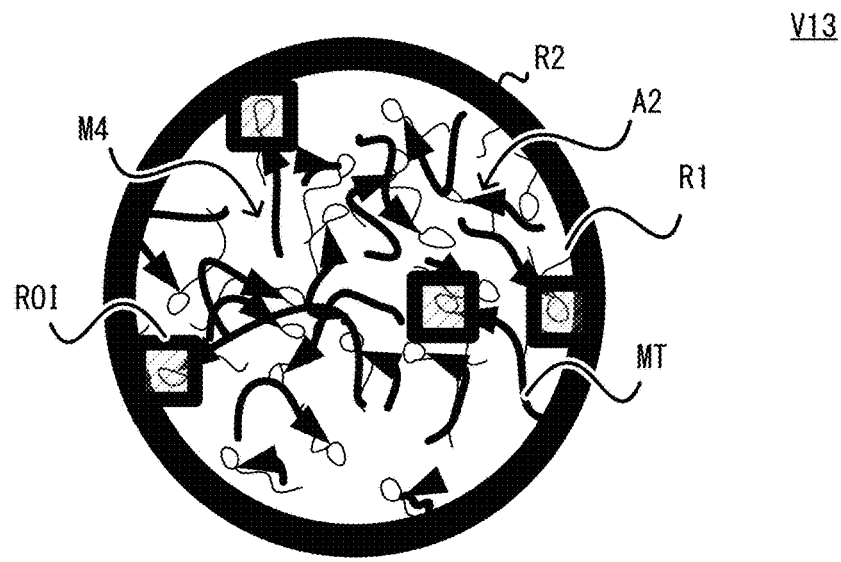
FIG. 21

MICROSCOPE SYSTEM AND PROJECTION UNIT

CROSS REFERENCE TO RELATED APPLICATIONS

This application is based upon and claims the benefit of priority of the prior Japanese Patent Application No. 2018-183763, filed Sep. 28, 2018, the entire contents of which are incorporated herein by reference.

This is a Continuation Application of PCT Application No. PCT/JP2018/047499, filed Dec. 25, 2018, which was not published under PCT Article 21(2) in English.

BACKGROUND OF THE INVENTION

Field of the Invention

The disclosures herein relate to a microscope system, and a projection unit.

Description of the Related Art

The whole slide imaging (WSI) technique has attracted attention as a technique for reducing the burden on pathologists in pathological diagnoses. The WSI technique is a technique for creating a whole slide image (WSI), which is a digital image of the entire area of a specimen on slide glass. A pathologic can enjoy various advantages by performing a diagnosis with a WSI, i.e., a digital image, displayed on a monitor. In particular, the advantages include the ones wherein the microscope body does not need to be operated during the diagnosis, the display magnification can be easily changed, and a plurality of pathologists can be concurrently involved in the diagnosis. Such a WSI technique is described in, for example, Japanese National Publication of International Patent Application No. 2001-519944.

SUMMARY OF THE INVENTION

A microscope system in accordance with an aspect of the present invention includes: an eyepiece; an objective that guides light from a sample to the eyepiece; a tube lens that is disposed on a light path between the eyepiece and the objective and forms an optical image of the sample on the basis of light therefrom; a projection apparatus that projects a projection image onto an image plane on which the optical image is formed; and a processor that performs processes. The processes include: performing, for digital image data of the sample, at least one analysis process selected from a plurality of analysis processes, the performing the at least one analysis process including outputting an analysis result corresponding to the at least one analysis process; and generating projection image data representing the projection image on the basis of the analysis result and the at least one analysis process. The projection image data indicates the analysis result in a display format corresponding to the at least one analysis process. The display format includes an image color. The generating the projection image data includes determining a color for the projection image in accordance with the at least one analysis process selected from the plurality of analysis processes.

A microscope system in accordance with another aspect of the invention includes: an eyepiece; an objective that guides light from a sample to the eyepiece; a tube lens that is disposed on a light path between the eyepiece and the objective and forms an optical image of the sample on the basis of light therefrom; a projection apparatus that projects a projection image onto an image plane on which the optical image is formed; and a processor that performs processes. The processes include: generating projection image data representing the projection image on the basis of a diagnosis protocol selected from a plurality of diagnosis protocols. The projection image data corresponds to the selected diagnosis protocol. The generating the projection image data includes determining a color for the projection image in accordance with the diagnosis protocol selected from the plurality of diagnosis protocols.

A microscope system in accordance with still another aspect of the invention includes: an eyepiece; an objective that guides light from a sample to the eyepiece; a tube lens that is disposed on a light path between the eyepiece and the objective and forms an optical image of the sample on the basis of light therefrom; a projection apparatus that projects first and second projection images onto an image plane on which the optical image is formed; and a processor that performs processes. The processes include: performing, for digital image data of the sample, at least one analysis process selected from a plurality of analysis processes and outputs an analysis result corresponding to the at least one analysis process; generating first projection image data representing the first projection image on the basis of the analysis result and the at least one analysis process; and generating second projection image data representing the second projection image on the basis of a diagnosis protocol selected from a plurality of diagnosis protocols. The first projection image data indicates the analysis result in a display format corresponding to the at least one analysis process. The second projection image data corresponds to the selected diagnosis protocol. The display format includes an image color. The generating first projection image data includes determining a color for the projection image in accordance with the at least one analysis process selected from the plurality of analysis processes.

A projection unit in accordance with an aspect of the invention is a projection unit for a microscope provided with an objective, a tube lens, and an eyepiece, the projection unit including: an imaging apparatus that acquires digital image data of a sample on the basis of light therefrom; a projection apparatus that projects a projection image onto an image plane on which an optical image of the sample is formed by the tube lens; and a processor that performs processes. The processes include: performing, for digital image data of the sample, at least one analysis process selected from a plurality of analysis processes, the performing the at least one analysis process including outputting an analysis result corresponding to the at least one analysis process, and generating projection image data representing the projection image on the basis of the analysis result and the at least one analysis process. The projection image data indicates the analysis result in a display format corresponding to the at least one analysis process. The display format includes an image color. The generating the projection image data includes determining a color for the projection image in accordance with the at least one analysis process selected from the plurality of analysis processes.

A projection unit in accordance with another aspect of the invention is a projection unit for a microscope provided with an objective, a tube lens, and an eyepiece, the projection unit including: an imaging apparatus that acquires digital image data of a sample on the basis of light therefrom; a projection apparatus that projects a projection image onto an image plane on which an optical image of the sample is formed by the tube lens; and a processor that performs processes. The processes include: generating projection image data representing the projection image on the basis of a diagnosis protocol selected from a plurality of diagnosis protocols. The projection image data corresponds to the selected diagnosis protocol. The generating the projection image data includes determining a color for the projection image in accordance with the diagnosis protocol selected from the plurality of diagnosis protocols.

BRIEF DESCRIPTION OF THE DRAWINGS

FIG. 4 exemplifies a selection screen 31;
FIG. 11 illustrates the configuration of a neural network;
FIG. 13 illustrates the configuration of a computer 60 included in a microscope system 3;
FIG. 19 illustrates the configuration of a diagnosis assistance system that includes a microscope system 4 and external browsing systems 300;
FIG. 21 illustrates examples of change in an image viewed through an eyepiece 104 in a microscope system that includes a microscope 500.

DESCRIPTION OF EMBODIMENTS

A system to which the WSI technique is applied (hereinafter, "WSI system") is required to have high performance. In particular, as information on colors or light and shade is highly important in a pathological diagnosis, the WSI system may be required to have a high color reproducibility and a wide dynamic range. Hence, the devices forming the WSI system need to have high performance and thus cannot help being expensive, and as a result, only limited users can introduce the WSI system.

In view of the abovementioned facts, there is demand for a new technique for reducing the burden on a pathologist by assisting in a pathological diagnosis performed by the pathologist on the basis of optical images (analog images) acquired by an optical microscope.

It is an object in one feature of the present invention to provide a diagnosis assistance technique for assisting in a pathological diagnosis performed by a pathologist on the basis of optical images.

Considering such circumstances, an embodiment of the present invention will be described hereinafter.

First Embodiment

Figure 1:
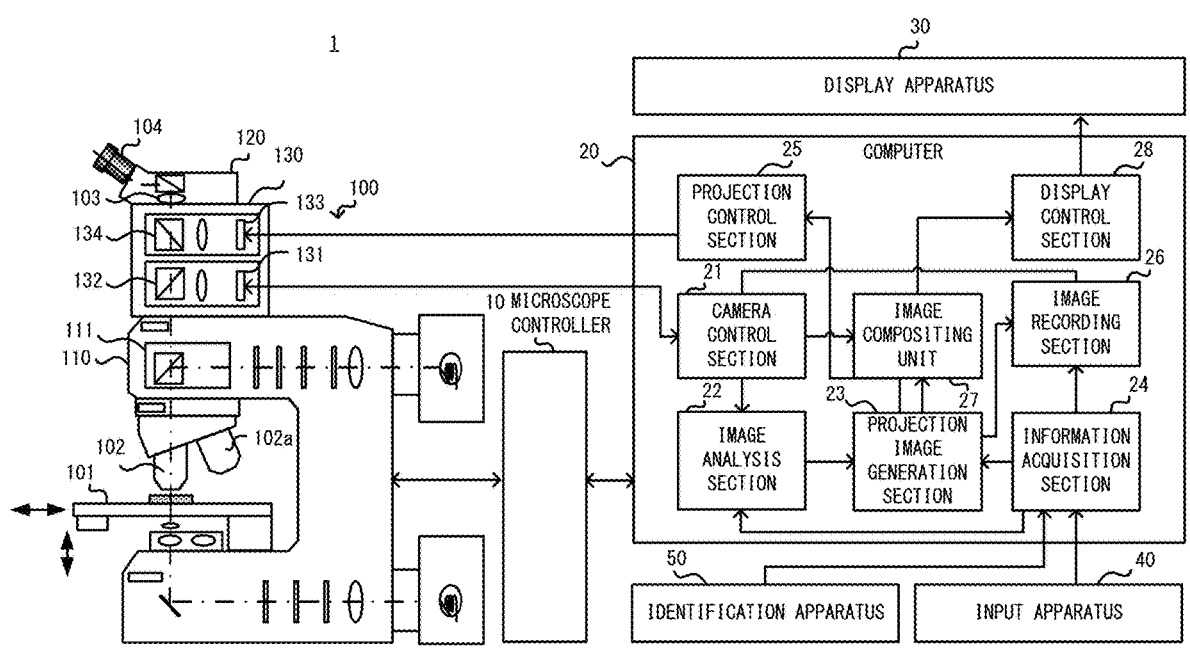
FIG. 1 illustrates the configuration of a microscope system 1.
Figure 2:
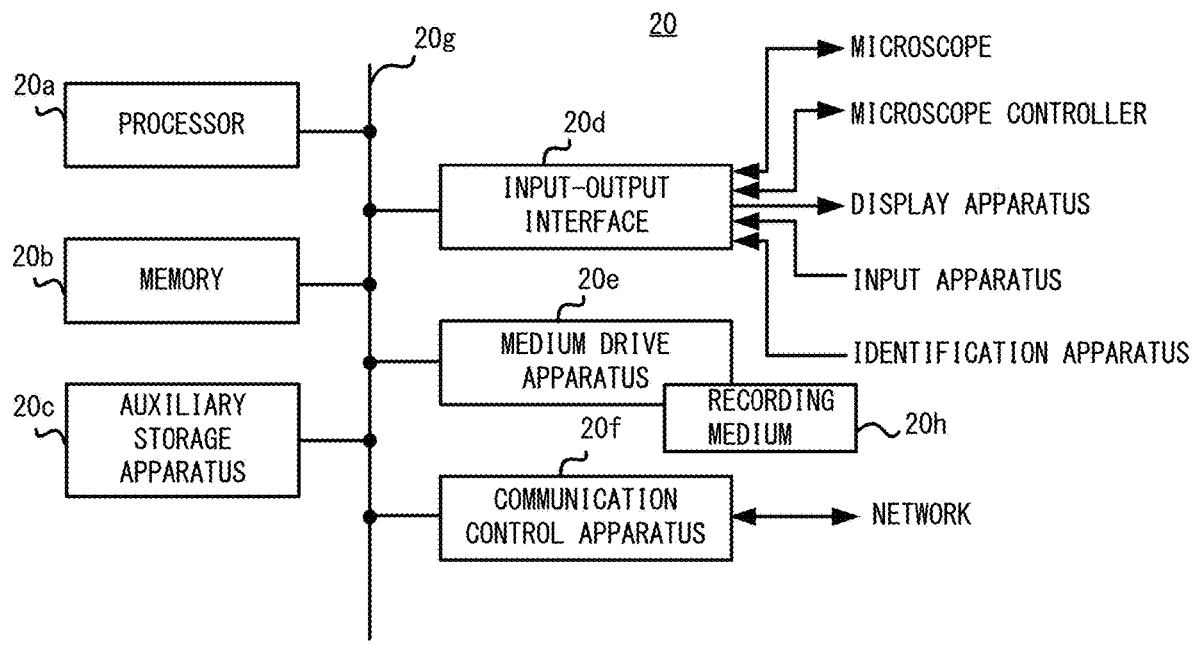
FIG. 2 illustrates the configuration of a computer 20.

FIG. 1 illustrates the configuration of a microscope system 1 in accordance with the present embodiment. FIG. 2 illustrates the configuration of a computer 20. The microscope system 1 is used by a pathologist in a pathological diagnosis and includes at least an objective 102, a tube lens 103, an eyepiece 104, an image analysis section 22, a projection image generation section 23, and a projection apparatus 133.

Using the projection apparatus 133, the microscope system 1 projects a projection image onto an image plane on which an optical image of a sample is formed by the objective 102 and the tube lens 103. More specifically, the image analysis section 22 performs an analysis process for digital image data of the sample, the projection image generation section 23 generates projection image data on the basis of the analysis result and the analysis process, and the projection apparatus 133 projects a projection image indicating the analysis result in a display format corresponding to the analysis process onto the image plane. Thus, the pathologist will view an image obtained by superimposing the projection image in a display format corresponding to the analysis process onto the optical image. Accordingly, the microscope system 1 can provide the pathologist observing a sample through the eyepiece 104 with various information for assistance in the pathological diagnosis in an easily viewable display format.

The following describes a specific example of the configuration of the microscope system 1 in detail by referring to FIGS. 1 and 2. As depicted in FIG. 1, the microscope system 1 includes a microscope 100, a microscope controller 10, a computer 20, a display apparatus 30, an input apparatus 40, and an identification apparatus 50.

For example, the microscope 100 may be an upright microscope and include a microscope body 110, a tube 120, an intermediate tube 130. Alternatively, the microscope 100 may be an inverted microscope.

The microscope body 110 includes a stage 101 on which a sample is placed, objectives (objectives 102 and 102a) that guide light from the sample to the eyepiece 104, an epi-illumination optical system, and a transmitted illumination optical system. The stage 101 may be a manual stage or a motorized stage. A revolver is desirably mounted with a plurality of objectives having different magnifications. For example, the objective 102 may have a 4-fold magnification, and the objective 102a may have a 20-fold magnification. The microscope body 110 may include at least either an epi-illumination optical system or a transmitted illumination optical system.

The microscope body 110 further includes a turret 111 for switching a microscopy. For example, the turret 111 may have disposed thereon a fluorescence cube to be used in a fluorescent observation method or a half mirror to be used in a bright field observation method. In addition, the microscope body 110 may be provided with an optical element to be used in a certain microscopy, in a manner such that this optical element can be inserted/removed into/from a light path. Specifically, for example, the microscope body 110 may include a DIC prism, polarizer, or analyzer to be used in a differential-interference-contrast observation method.

The tube 120 is a monocular or binocular tube mounted with the eyepiece 104. The tube lens 103 is provided within the tube 120. The tube lens 103 is disposed on a light path between the objective 102 and the eyepiece 104. On the basis of light from a sample, the tube lens 103 forms an optical image of the sample on an image plane between the eyepiece 104 and the tube lens 103. The tube lens 103 also forms a projection image on the image plane on the basis of light from the projection apparatus 133 (descriptions will be given of the projection image hereinafter). Thus, the projection image is superimposed onto the optical image on the image plane.

The intermediate tube 130 is provided between the microscope body 110 and the tube 120. The intermediate tube 130 includes an image sensor 131, a light deflection element 132, the projection apparatus 133, and a light deflection element 134.

The image sensor 131 is an example of a photodetector that detects light from a sample. The image sensor 131 is a two-dimensional image sensor, e.g., CCD image sensor, CMOS image sensor. The image sensor 131 detects light from a sample and generates digital image data thereof on the basis of the detection result.

The light deflection element 132 is an example of a first light deflection element that deflects light from a sample toward the image sensor 131. For example, the light deflection element 132 may be a beam splitter such as a half mirror. A variable beam splitter capable of varying transmittance and reflectance may be used for the light deflection element 132. The light deflection element 132 is disposed on the light path between the eyepiece 104 and the objective 102. Thus, the image sensor 131 can acquire a digital image of the sample as seen in the same direction as a visual observation.

The projection apparatus 133 projects a projection image (described hereinafter) onto an image plane in accordance with an instruction from the computer 20. For example, the projection apparatus 133 may be a projector using a liquid crystal device, a projector using a digital mirror device, or a projector using an LCOS.

The light deflection element 134 is an example of a second light deflection element that deflects light emitted from the projection apparatus 133 toward an image plane. For example, the light deflection element 134 may be a beam splitter such as a half mirror. A variable beam splitter capable of varying transmittance and reflectance may be used for the light deflection element 134. A dichroic mirror may be used for the light deflection element 134. The light deflection element 134 is disposed on the light path between the image plane and the light deflection element 132. Thus, light from the projection apparatus 133 can be prevented from being incident on the image sensor 131.

The microscope controller 10 controls the microscope 100, in particular the microscope body 110. The microscope controller 10 is connected to the computer 20 and the microscope 100 and controls the microscope 100 in accordance with an instruction from the computer 20.

For example, the display apparatus 30 may be a liquid crystal display, an organic electroluminescence (OLED) display, or a cathode ray tube (CRT) display. The input apparatus 40 outputs, to the computer 20, an operation signal that corresponds to an input operation performed by the user.

The input apparatus 40 is, for example, a keyboard and may include a mouse, a joystick, or a touch panel.

The identification apparatus 50 acquires identification information assigned to a sample. The identification information includes at least information identifying the sample. The identification information may include information pertaining to a method of analyzing the sample and a diagnosis protocol. For example, the identification apparatus 50 may be a bar code reader, an RFID reader, or a QR® code reader.

The computer 20 controls the entirety of the microscope system 1. The computer 20 is connected to the microscope 100, the microscope controller 10, the display apparatus 30, the input apparatus 40, and the identification apparatus 50. As depicted in FIG. 1, the computer 20 includes a camera control section 21, an image analysis section 22, a projection image generation section 23, an information acquisition section 24, a projection control section 25, an image recording section 26, an image compositing section 27, and a display control section 28 as components pertaining primarily to the controlling of the projection apparatus 133.

The camera control section 21 acquires digital image data of a sample by controlling the image sensor 131. The digital image data acquired by the camera control section 21 is output to the image analysis section 22, the image recording section 26, and the image compositing section 27.

The image analysis section 22 performs, for the digital image data acquired by the camera control section 21, at least one analysis process selected from a plurality of analysis processes and outputs an analysis result corresponding to the at least one analysis process to the projection image generation section 23. The plurality of analysis processes subjected to selection may be processes intended for a plurality of different staining methods such as HE staining and IHC staining. Alternatively, the plurality of analysis processes subjected to selection may be processes intended for a plurality of different biomarkers such as HER2, Ki-67, and ER/PgR. The plurality of analysis processes subjected to selection may also be processes intended for a plurality of different combinations of staining methods and biomarkers.

The image analysis section 22 may select at least one analysis process on the basis of an input operation performed by the user. More specifically, the image analysis section 22 may select at least one analysis process on the basis of operation information of the user acquired by the information acquisition section 24. Alternatively, the image analysis section 22 may select at least one analysis process on the basis of identification information acquired by the identification apparatus 50. More specifically, identification information acquired by the identification apparatus 50 may be acquired from the information acquisition section 24, and at least one analysis process may be selected on the basis of an analysis method included in the identification information. The operation information and the identification information both include information for selecting an analysis process. Accordingly, both of these pieces of information are hereinafter referred to as selection information.

Details of the analysis processes performed by the image analysis section 22 are not particularly limited. For example, the image analysis section 22 may classify one or more structures seen in a digital image represented by digital image data into one or more classes and generate an analysis result including position information specifying the position of a structure classified into at least one class of the one or more classes. More specifically, the image analysis section 22 may classify the cells seen in a digital image according to the staining intensities and generate an analysis result including class information indicating the classes of the cells and position information specifying the outlines of the cells or the outlines of the nuclei of the cells. Alternatively, the image analysis section 22 may generate an analysis result including class information and position information as well as statistical information of structures classified into each at least one class, such as the number of cells of each class or the ratio of the cells of each class with reference to all cells. The structure classified into at least one class is desirably an object that serves as a basis for a judgment to be made by the pathologist in a pathological diagnosis.

The projection image generation section 23 generates projection image data on the basis of an analysis result output from the image analysis section 22 and at least one analysis process specified by selection information acquired from the information acquisition section 24. A projection image represented by the projection image data indicates the analysis result in a display format corresponding to the at least one analysis process. The projection image generated by the projection image generation section 23 is output to the projection control section 25, the image recording section 26, and the image compositing section 27.

A display format includes at least an image color. Thus, the projection image generation section 23 determines a color for a projection image in accordance with at least one analysis process. In addition to an image color, the display format may include the form of a graphic pattern (e.g., lines) forming an image. Accordingly, in accordance with the at least one analysis process, the projection image generation section 23 may determine a form for the graphic pattern forming the projection image. The form of the graphic pattern includes information on whether to paint over the inside of the graphic pattern, the type of the graphic pattern, and the like. For example, when a graphic pattern is a line, the line form may include a line type and a line thickness. In addition, a display format may include an image color as well as an image position. Accordingly, in accordance with at least one analysis process, the projection image generation section 23 may determine a positional relationship between a projection image and an optical image to be attained on an image plane or determine whether at least a portion of the projection image is to be projected onto an outside of the optical image.

More specifically, the projection image generation section 23 generates projection image data such that the color of a projection image is different from that of an optical image. As the color of an optical image varies according to what staining method is used, the projection image generation section 23 may change the color of a projection image in accordance with a staining method for which a selected analysis process is intended. In the case of, for example, HE staining, an optical image is colored in bluish purple, and thus the color of a projection image is desirably different from bluish purple.

As different portions within cells are stained according to what biomarker is used, the projection image generation section 23 may change the form of a graphic pattern forming a projection image in accordance with a biomarker for which a selected analysis process is intended. When, for example, analyzing overexpression of HER2 protein, cell membranes will be stained, and thus a projection image may be formed using an outline-formed graphic pattern clarifying the outlines of cells. When analyzing expression of ER/PgR, cell nuclei will be stained, and thus a projection image may be formed using a graphic pattern painting over the insides of the cell nuclei.

In addition, HE staining is often used to observe cell morphologies. When observing a cell morphology in detail, observation of an optical image is desirably not interfered with by a projection image. Accordingly, the projection image generation section 23 may change the position of the projection image in accordance with a staining method for which a selected analysis process is intended. In the case of HE staining, for example, when a projection image includes supplemental textual information, the position of the projection image may be changed to reduce overlap between the textual information and an optical image.

The information acquisition section 24 acquires information from an apparatus outside the computer 20. In particular, the information acquisition section 24 acquires operation information of the user on the basis of an operation signal from the input apparatus 40. The information acquisition section 24 also acquires identification information from the identification apparatus 50.

The projection control section 25 controls projection of a projection image onto the image plane by controlling the projection apparatus 133. The projection control section 25 may control the projection apparatus 133 in accordance with the setting of the microscope system 1. Specifically, the projection control section 25 may determine in accordance with the setting of the microscope system 1 whether to project a projection image onto the image plane, or may control the projection apparatus 133 such that the projection apparatus 133 projects a projection image onto the image plane when the microscope system 1 is in a predetermined setting. Thus, in accordance with the setting, the microscope system 1 can make a change as to whether to project a projection image onto the image plane.

The image recording section 26 records digital image data and projection image data. In particular, the image recording section 26 records, in a different region from the digital image data, the projection image data in association with the digital image data. Thus, the digital image data and the projection image data that are associated with each other can be individually read according to need. In addition, the image recording section 26 may acquire identification information assigned to the sample via the identification apparatus 50 and the information acquisition section 24, and record the acquired identification information in association with digital image data. The image recording section 26 may also record digital image data and projection image data when detecting input of a record instruction from the user.

The image compositing section 27 generates image data for a composite image obtained by compositing a digital image and a projection image on the basis of digital image data and projection image data and outputs the generated image data to the display control section 28.

The display control section 28 displays a composite image on the display apparatus 30 on the basis of composite image data output from the image compositing section 27. Alternatively, the display control section 28 may display a digital image alone on the display apparatus 30 on the basis of digital image data.

The computer 20 may be a general-purpose or special-purpose apparatus. For example, the computer 20 may have, but is not particularly limited to, a physical configuration such as that depicted in FIG. 2. Specifically, the computer 20 may include a processor 20a, a memory 20b, an auxiliary storage apparatus 20c, an input-output interface 20d, a medium drive apparatus 20e, and a communication control apparatus 20f, all of which may be connected to each other by a bus 20g.

For example, the processor 20a may be any processing circuit that includes a central processing unit (CPU). The processor 20a may implement the above-described components pertaining to the controlling of the projection apparatus 133 (e.g., camera control section 21, image analysis section 22, projection image generation section 23) by performing programmed processes by executing programs stored in the memory 20b, the auxiliary storage apparatus 20c, and a storage medium 20h. The processor 20a may be configured using a special-purpose processor such as an ASIC or an FPGA.

The memory 20b is a working memory for the processor 20a. For example, the memory 20b may be any semiconductor memory such as a random access memory (RAM). The auxiliary storage apparatus 20C is a nonvolatile memory such as an erasable programmable ROM (EPROM) or a hard disc drive. The input-output interface 20d communicates information with an external apparatus (microscope 100, microscope controller 10, display apparatus 30, input apparatus 40, identification apparatus 50).

The medium drive apparatus 20e can output data stored in the memory 20b or the auxiliary storage apparatus 20c to the storage medium 20h and read a program, data, and the like from the storage medium 20h. The storage medium 20h may be any portable recording medium. For example, the storage medium 20h may include an SD card, a universal serial bus (USB) flash memory, a compact disc (CD), and a digital versatile disc (DVD).

The communication control apparatus 20f inputs/outputs information to/from a network. For example, a network interface card (NIC) or a wireless local area network (wireless LAN) card may be used as the communication control apparatus 20f. The bus 20g connects the processor 20a, the memory 20b, the auxiliary storage apparatus 20c, and the like to each other in a manner such that data can be communicated therebetween.

Figure 3:
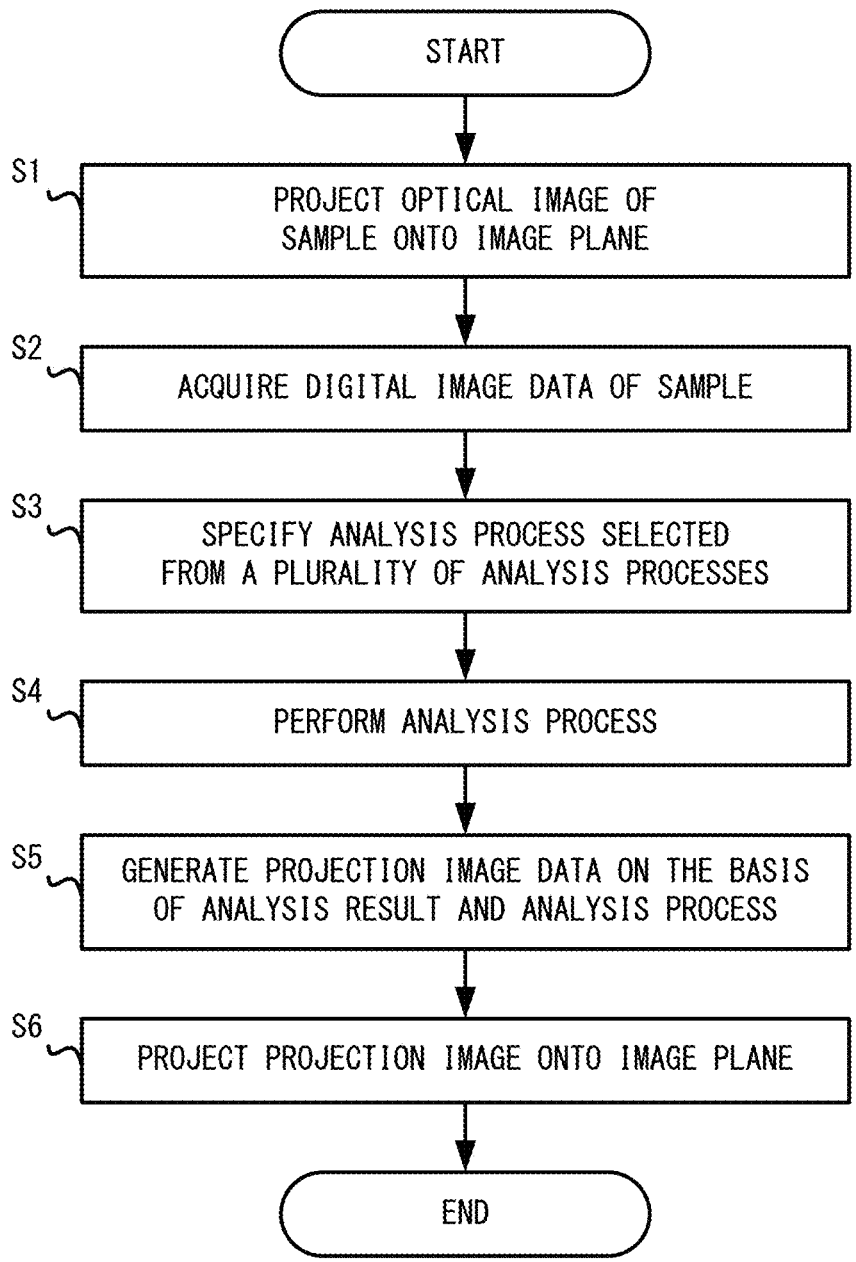
FIG. 3 is a flowchart of an image projection process performed by a microscope system 1.

The microscope system 1 configured as described above performs an image projection process depicted in FIG. 3. FIG. 3 is a flowchart of an image projection process performed by the microscope system 1. FIG. 4 exemplifies a selection screen 31. The following describes an image projection method implemented by the microscope system 1 by referring to FIGS. 3 and 4.

First, the microscope system 1 projects an optical image of a sample onto an image plane (step S1). In this example, the tube lens 103 focuses light the objective 102 receives from the sample onto the image plane, thereby forming an optical image of the sample.

In addition, the microscope system 1 acquires digital image data of the sample (step S2). In this example, the light deflection element 132 deflects a portion of the light the objective 102 receives from the sample toward the image sensor 131. The image sensor 131 generates the digital image data by imaging the sample on the basis of the light deflected by the light deflection element 132.

Then, the microscope system 1 specifies an analysis process selected from a plurality of analysis processes prepared in advance (step S3). In this example, the user may select, for example, menus on the selection screen 31 depicted in FIG. 4 (menus 32, 33, 34, and 35) and then click a button 36. The image analysis section 22 specifies the analysis process selected on the basis of the input operation performed by the user.

Upon an analysis process being specified, the microscope system 1 performs the specified analysis process (step S4). In this example, the image analysis section 22 obtains an analysis result by performing the analysis process selected in step S3 for the digital image data acquired in step S2.

The microscope system 1 generates projection image data on the basis of the analysis result obtained in step S4 and the analysis process specified in step S3 (step S5). In this example, the projection image generation section 23 generates projection image data representing a projection image displaying the analysis result obtained in step S4 in a display format corresponding to the analysis process specified in step S3.

Finally, the microscope system 1 projects the projection image onto the image plane (step S6). The projection control section 25 controls the projection apparatus 133 on the basis of the projection image data, thereby causing the projection apparatus 133 to project the projection image onto the image plane. Thus, the projection image is superimposed onto the optical image of the sample.

The microscope system 1 is such that an image analysis result provided by a computer is displayed on an optical image. Thus, during a pathological diagnosis based on an optical image of a sample, the pathologist can obtain various information for assisting in the diagnosis without taking the eye from the eyepiece. Meanwhile, the image analysis section 22 performs an analysis process selected from a plurality of analysis processes, so that the microscope system 1 can deal with various types of diagnoses. In addition, a projection image projected by the projection apparatus 133 has a display format corresponding to the analysis process. Accordingly, the microscope system 1 can provide the pathologist with various information for assistance in the pathological diagnosis in an easily viewable display format. Hence, the microscope system 1 can assist in a pathological diagnosis based on optical images and reduce the task burden on the pathologist.

Furthermore, the microscope system 1 assists in a pathological diagnosis by displaying additional information (projection image) on an optical image. Thus, expensive devices are not necessary, unlike WSI systems which perform pathological diagnoses based on digital images. Hence, the microscope system 1 can reduce the burden on the pathologist with substantial rise in device cost avoided. Meanwhile, when a pathological diagnosis is performed using a WSI system, whole slide images (WSIs) will need to be created in advance; and in the case of the microscope system 1, no advance preparations need to be made, and diagnosis tasks can be started immediately.

FIGS. 5-10 exemplify images each viewed through the eyepiece 104 in the microscope system 1. By referring to FIGS. 5-10, the following specifically describes how an observation is performed using the microscope system 1 executing the image projection process depicted in FIG. 3.

Figure 5:
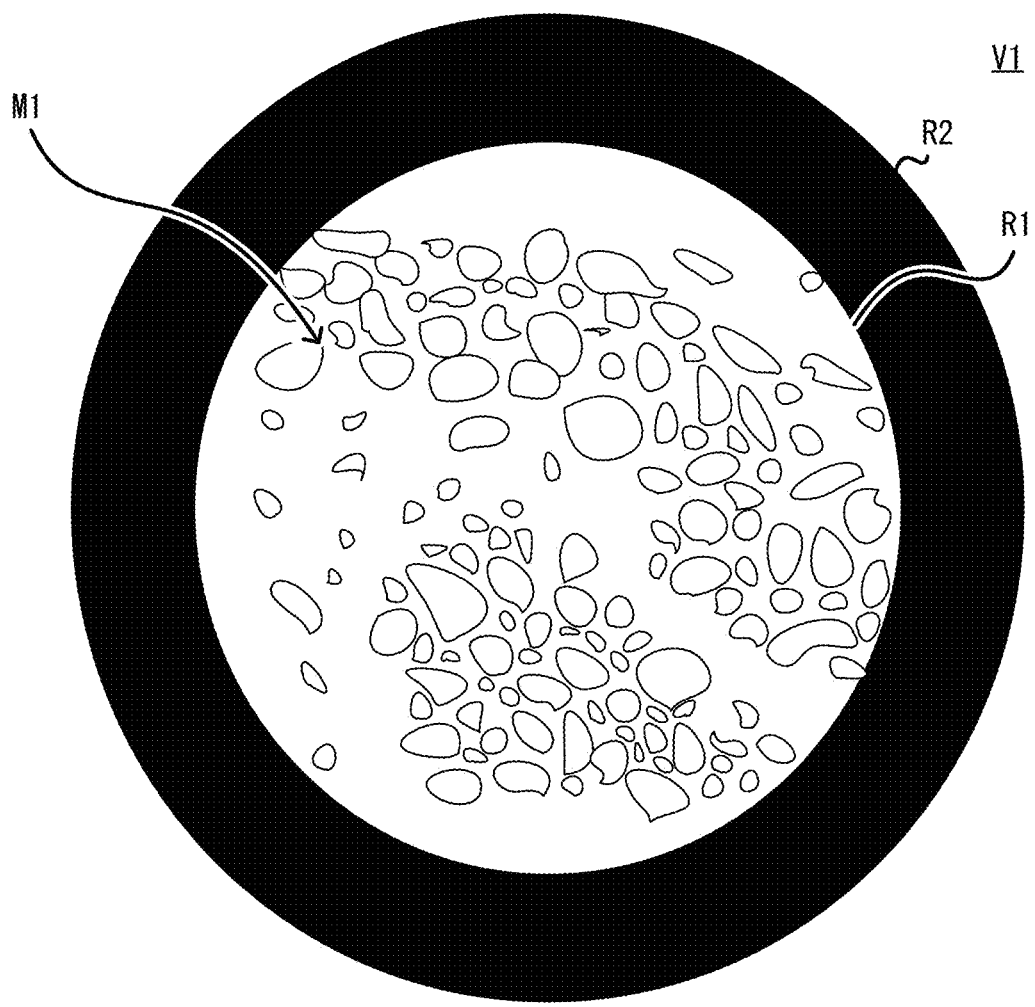
FIG. 5 illustrates an example of an image viewed through an eyepiece 104 in a microscope system 1.
Figure 6:
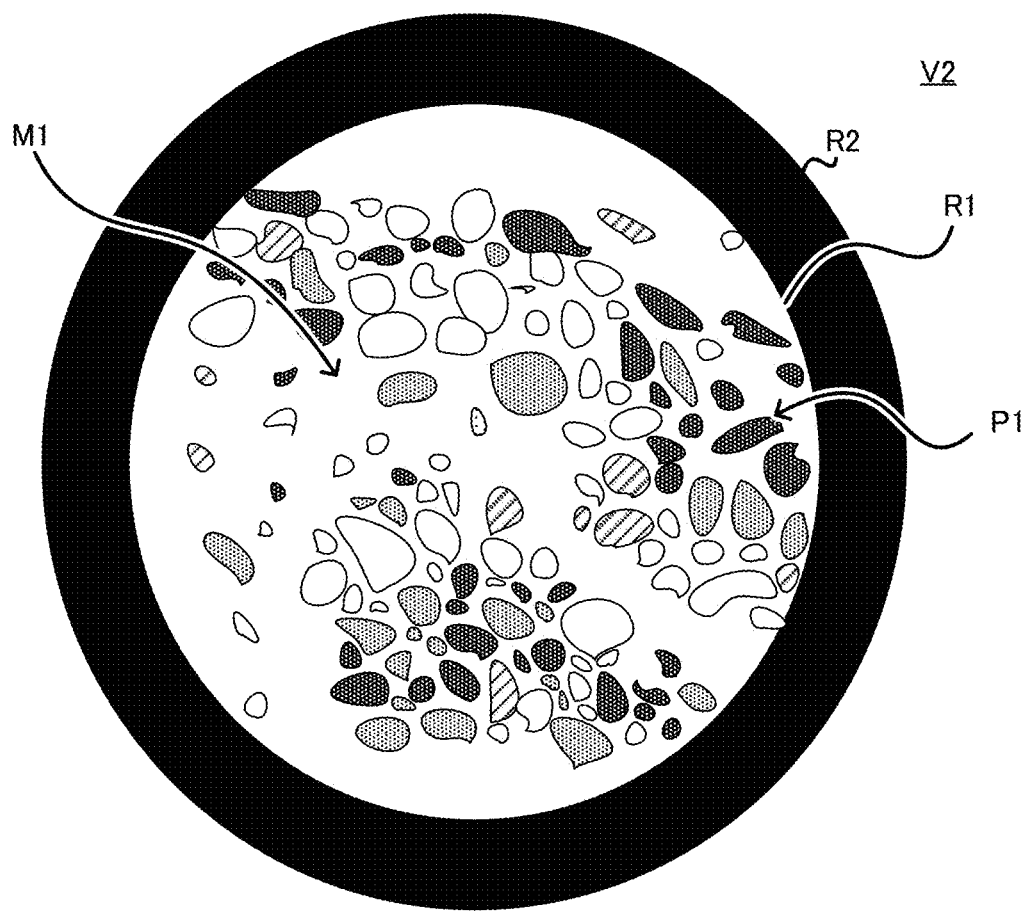
FIG. 6 illustrates another example of an image viewed through an eyepiece 104 in a microscope system 1.
Figure 7:
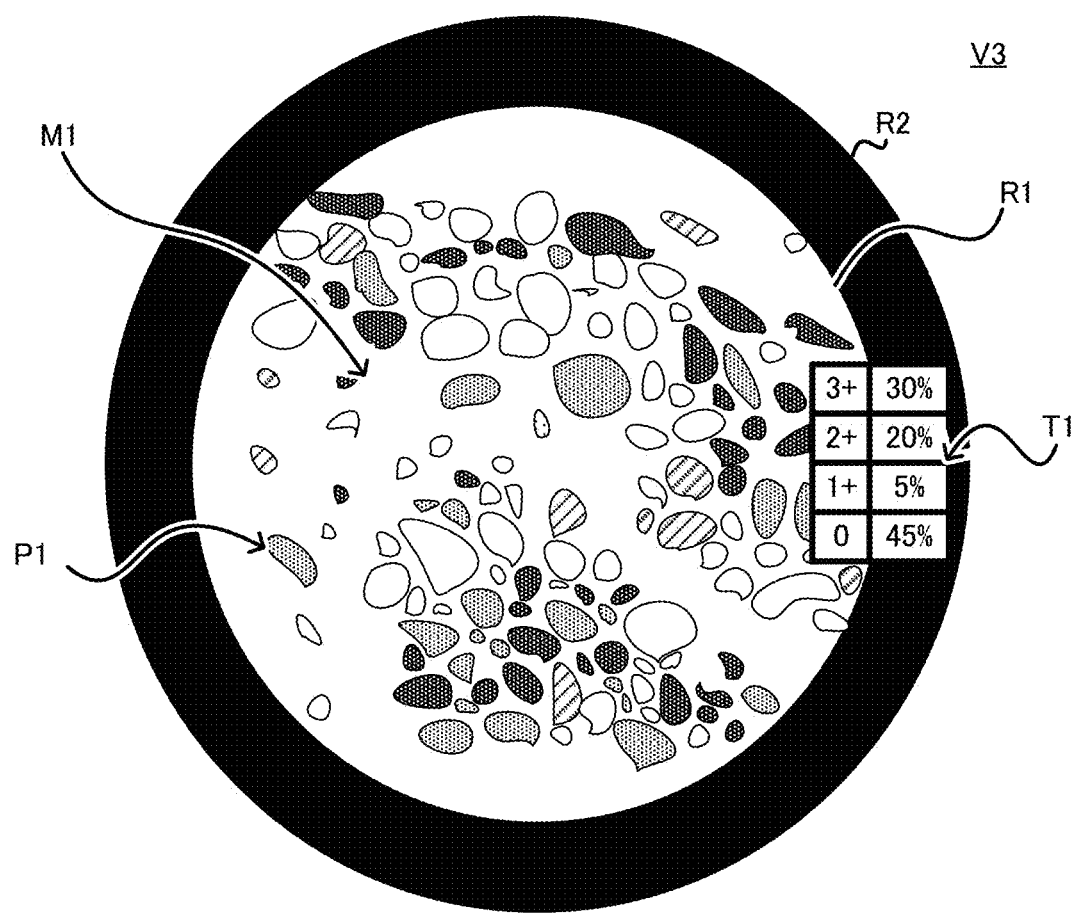
FIG. 7 illustrates still another example of an image viewed through an eyepiece 104 in a microscope system 1.

First, with reference to FIGS. 5-7, descriptions are given of a situation in which a "cytologic diagnosis," a "breast cancer," an "IHC staining," and an "ER/PgR" are selected within the selection screen 31 depicted in FIG. 4.

After an observation using the microscope system 1 is started, the pathologist can observe an image V1 depicted in FIG. 5 by looking through the eyepiece 104. The image V1 is an optical image M1 formed on an image plane and corresponding to the actual field of view. Stained nuclei of cancer cells are seen in the image V1. A dark region R2 is present around a region R1 onto which the image V1 is projected. The region R2 is included in the region on the image plane that can be observed through the eyepiece 104, and light from the objective 102 cannot pass through the region R2. In this case, the display apparatus 30 may display an image corresponding to the image V1 on the basis of digital image data generated by the image sensor 131.

Then, the computer 20 analyzes the digital image data. Cell nuclei are specified through the analysis and classified in accordance with the staining intensities. For example, unstained nuclei may be classified into a class 0 indicating negative. Weakly stained nuclei may be classified into a class 1+ indicating weakly positive. Moderately stained nuclei may be classified into a class 2+ indicating medium positive. Strongly stained nuclei may be classified into a class 3+ indicating strongly positive.

The computer 20 generates projection image data on the basis of the analysis result. The projection apparatus 133 projects a projection image represented by the projection image data onto the image plane. The projection image represented by the projection image data includes a position image formed from a graphic pattern indicating the positions of the classified cell nuclei. The graphic pattern has a different color for each of the classes.

When the projection apparatus 133 projects the projection image, the pathologist can observe an image V2 depicted in FIG. 6. The image V2 is obtained by superimposing a projection image including the position image P1 onto the optical image M1. In this case, the display apparatus 30 may display an image corresponding to the image V2. The staining states of the cells in the image V2 depicted in FIG. 6 can be determined more easily than those in the image V1 (optical image M1) depicted in FIG. 5. Hence, a score calculation based on a predetermined scoring method such as the J-score used in the pathological diagnose is facilitated. Accordingly, the microscope system 1 can assist in the task of positive/negative determination performed by the pathologist, thereby reducing the burden on the pathologist.

The projection image represented by the projection image data may include, in addition to the position image P1, a statistical image T1 formed from statistical information of the classified cells. In this case, the pathologist can observe an image V3 depicted in FIG. 7. The image V3 is obtained by superimposing the projection image including the position image P1 and the statistical image T1 onto the optical image M1. In this case, the display apparatus 30 may display an image corresponding to the image V3. The score calculation for the image V3 depicted in FIG. 7 is further facilitated owing to the statistical image T1. Accordingly, the microscope system 1 can better assist in the task of positive/negative determination performed by the pathologist, thereby further reducing the burden on the pathologist.

The thresholds for the scoring determinations of 0, 1+, 2+, and 3+ indicating the degrees of staining intensities may vary depending on individual pathologists, the guidelines adopted in hospital facilities, or the diagnostic criteria in individual countries. In view of this, an optical image M1 may be compared with a position image P1 and a statistical image T1, and if a question arises as to the statistical image T1 based on an analysis result, the observer may change a threshold used in the analysis process by using an input apparatus. A new analysis process can be performed on the basis of the threshold after change, and the user can check a new statistical image T1' in which the result of the new analysis process is reflected in real time, thereby receiving better assistance in the task of setting an appropriate threshold. Hence, the burden on the pathologist can be further reduced.

Figure 8:
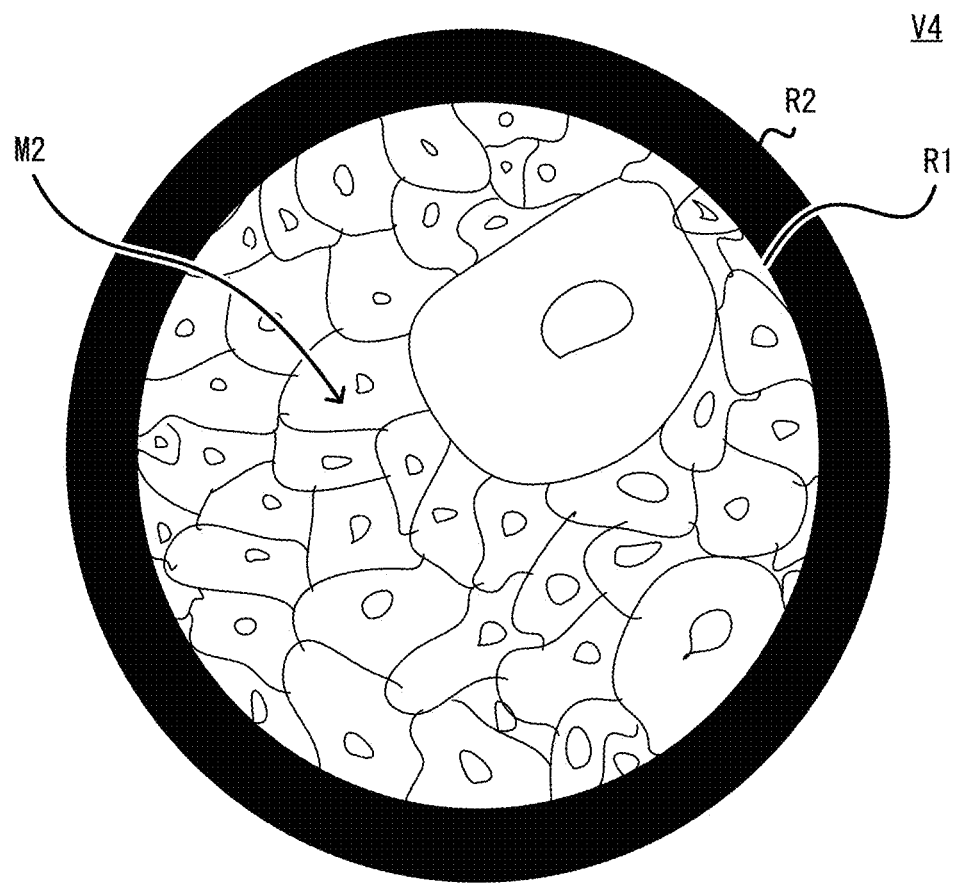
FIG. 8 illustrates yet another example of an image viewed through an eyepiece 104 in a microscope system 1.
Figure 9:
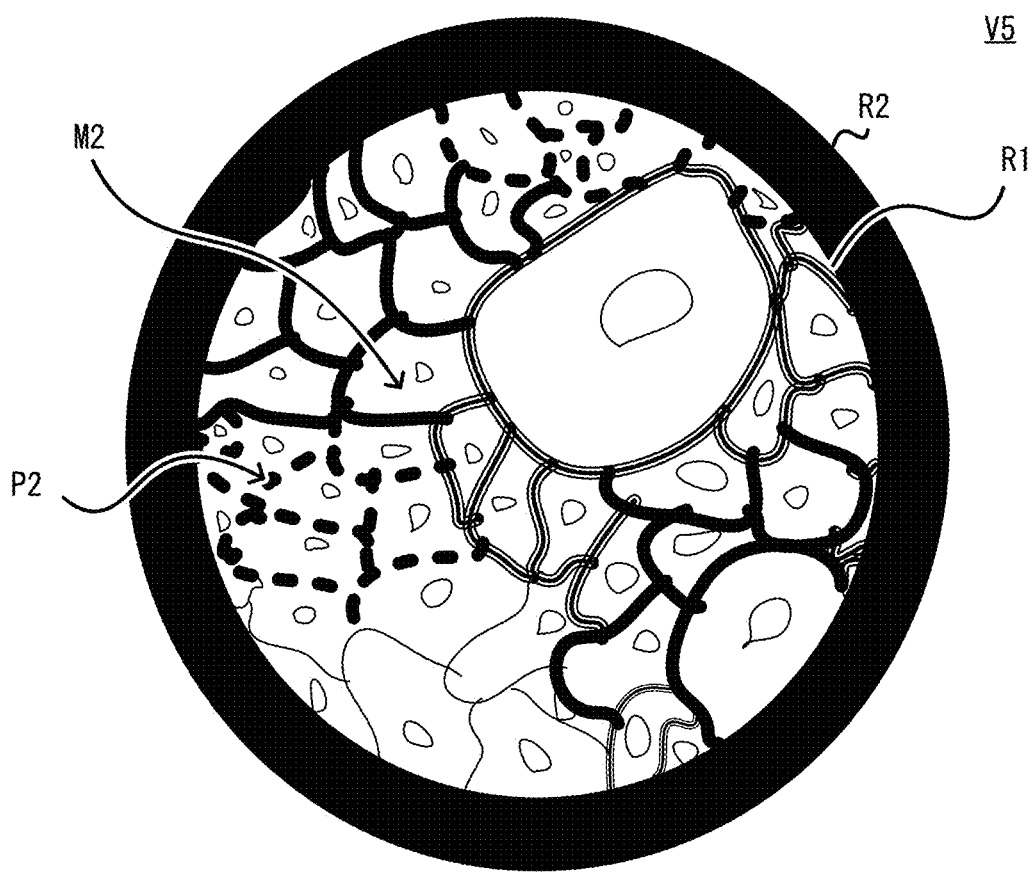
FIG. 9 illustrates a further example of an image viewed through an eyepiece 104 in a microscope system 1.
Figure 10:
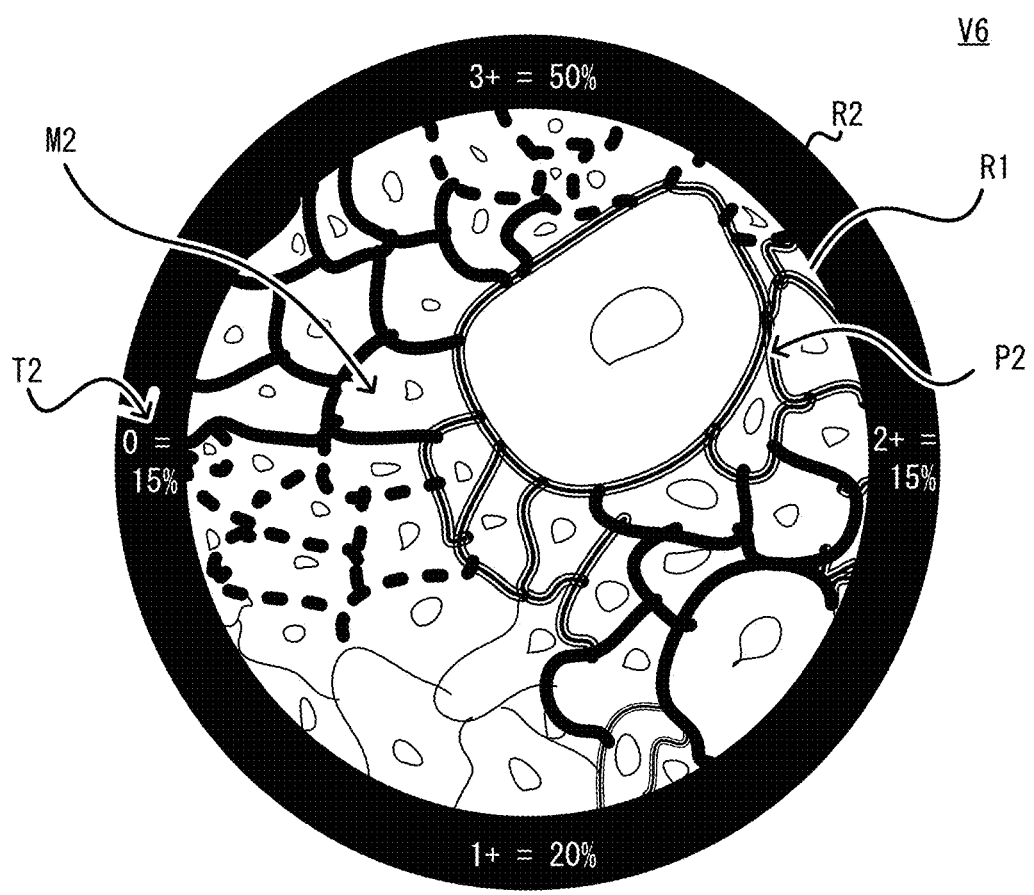
FIG. 10 illustrates still further example of an image viewed through an eyepiece 104 in a microscope system 1.

Next, with reference to FIGS. 8-10, descriptions are given of a situation in which the "cytologic diagnosis," the "breast cancer," the "IHC staining," and an "HER2" are selected within the selection screen 31 depicted in FIG. 4.

After an observation using the microscope system 1 is started, the pathologist can observe an image V4 depicted in FIG. 8 by looking through the eyepiece 104. The image V4 is an optical image M2 formed on an image plane and corresponding to the actual field of view. Stained cell membranes of cancer cells are seen in the image V4. In this case, the display apparatus 30 may display an image corresponding to the image V4 on the basis of digital image data generated by the image sensor 131.

Then, the computer 20 analyzes the digital image data. Cell membranes are specified through the analysis and classified in accordance with the staining intensities and the staining patterns. For example, cells with membranes unstained at all may be classified into a class 0 indicating negative. Cells with membranes partly or weakly stained may be classified into a class 1+ indicating weakly positive. Cells with membranes moderately stained through the entirety thereof may be classified into a class 2+ indicating medium positive. Cells with membranes strongly stained through the entirety thereof may be classified into a class 3+ indicating strongly positive.

The computer 20 generates projection image data on the basis of the analysis result. The projection apparatus 133 projects a projection image represented by the projection image data onto the image plane. The projection image represented by the projection image data includes a position image P2 formed from a graphic pattern indicating the positions of the classified cells. The graphic pattern has a different form (line type) for each of the classes.

When the projection apparatus 133 projects the projection image, the pathologist can observe an image V5 depicted in FIG. 9. The image V5 is obtained by superimposing a projection image including the position image P2 onto the optical image M2. In this case, the display apparatus 30 may display an image corresponding to the image V5. The staining states of the cell membranes in the image V5 depicted in FIG. 9 can be determined more easily than those in the image V4 (optical image M2) depicted in FIG. 8. Hence, a score calculation based on a predetermined scoring method used in the pathological diagnosis is facilitated. Accordingly, the microscope system 1 can assist in the task of positive/negative determination performed by the pathologist, thereby reducing the burden on the pathologist.

The projection image represented by the projection image data may include, in addition to the position image P2, a statistical image T2 formed from statistical information of the classified cells. In this case, the pathologist can observe an image V6 depicted in FIG. 10. The image V6 is obtained by superimposing a projection image including the position image P2 and the statistical image T2 onto the optical image M2. In this example, the statistical image T2 is projected onto an outside of a region R1 through which a pencil of light from the objective 102 passes. In this case, the display apparatus 30 may display an image corresponding to the image V6. The score calculation for the image V6 depicted in FIG. 10 is further facilitated owing to the statistical image T2. Accordingly, the microscope system 1 can better assist in the task of positive/negative determination performed by the pathologist, thereby further reducing the burden on the pathologist.

FIGS. 5-10 exemplify projection images that are formed in different forms (line types, whether there are portions painted over) of graphic patterns and thus displayed in display formats different from each other. However, projection images may have different image colors in accordance with analysis processes.

The image analysis section 22 in the microscope system 1 may perform a plurality of analysis processes using a plurality of predetermined algorithms or may perform a plurality of analysis processes using a plurality of trained neural networks.

Parameters for each of the plurality of trained neural networks may be generated by training a neural network by means of a different apparatus from the microscope system 1. The computer 20 may download and apply the generated parameters to the image analysis section 22. The computer 20 may download a parameter for a new neural network so as to add, on an as-needed basis, an analysis process that can be selected by the image analysis section 22.

FIG. 11 illustrates the configuration of a neural network NN. The neural network NN includes an input layer, a plurality of intermediate layers, and an output layer. Output data D2 output from the output layer by inputting input data D1 to the input layer is compared with correct answer data D3. Then, learning is performed using an error back propagation method so as to update the parameters for the neural network NN. Note that a set of input data D1 and correct answer data D3 is training data for supervised learning.

Second Embodiment

Figure 12:
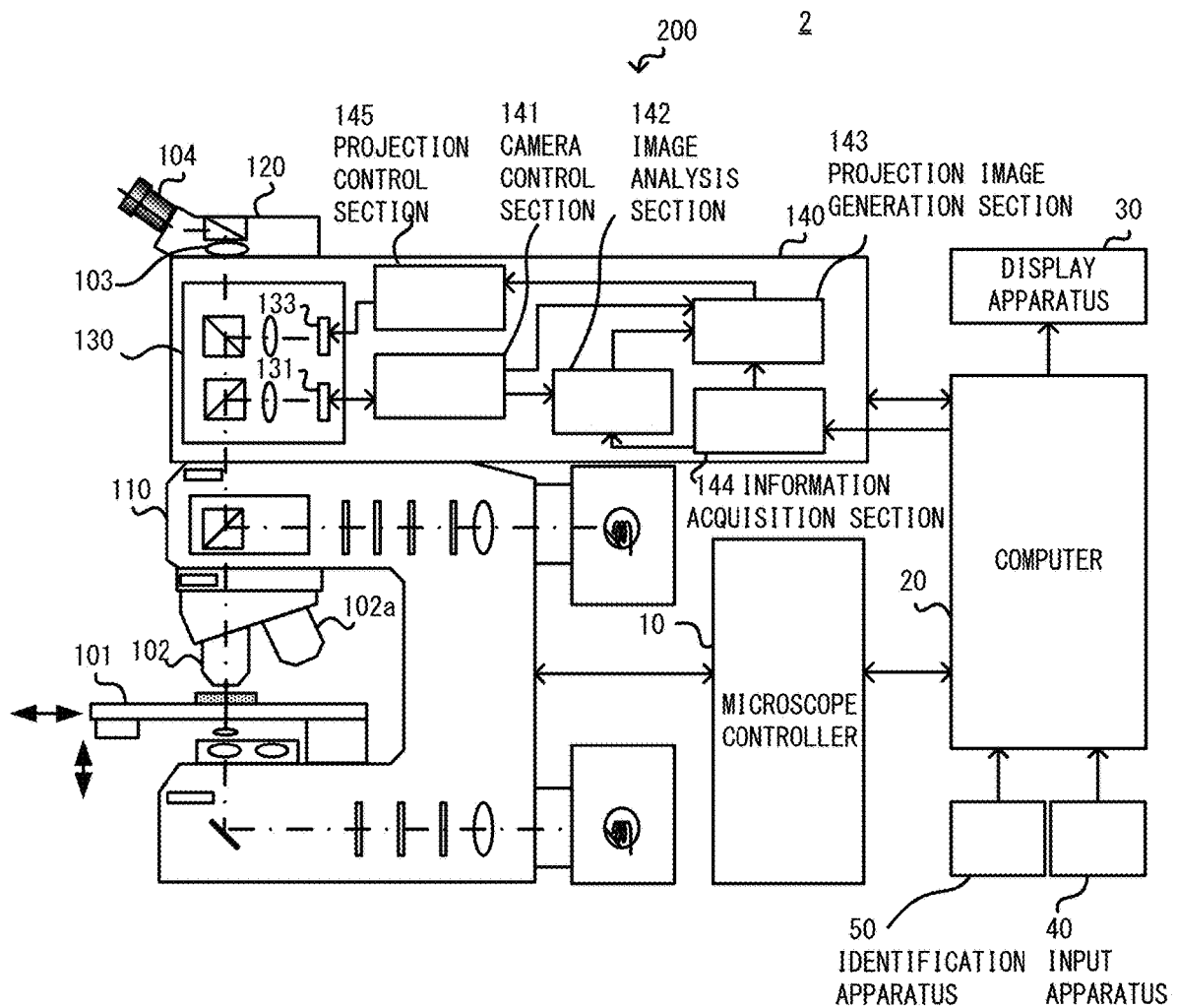
FIG. 12 illustrates the configuration of a microscope system 2.

FIG. 12 illustrates the configuration of a microscope system 2 in accordance with the present embodiment. The microscope system 2 is different from the microscope system 1 in that the former includes a microscope 200 in place of the microscope 100. The microscope 200 includes a projection unit 140 between the microscope body 110 and the tube 120.

The projection unit 140, which is a projection unit for a microscope provided with the objective 102, the tube lens 103, and the eyepiece 104, includes the intermediate tube 130. Thus, the projection unit 140 includes the image sensor 131, i.e., an example of an imaging apparatus that acquires digital image data of a sample on the basis of light therefrom, and the projection apparatus 133 that projects a projection image onto an image plane on which an optical image is formed.

The projection unit 140 further includes an image analysis section 142 and a projection image generation section 143. The projection unit 140 may include a camera control section 141, an information acquisition section 144, and a projection control section 145.

The camera control section 141, the image analysis section 142, the projection image generation section 143, and the projection control section 145 are respectively similar to the camera control section 21, the image analysis section 22, the projection image generation section 23, and the projection control section 25. Accordingly, detailed descriptions thereof are omitted herein.

The information acquisition section 144 obtains operation information of the user on the basis of an operation signal acquired via the computer 20 from the input apparatus 40. The information acquisition section 144 acquires identification information from the identification apparatus 50 via the computer 20.

In the present embodiment, similar effects to the microscope system 1 can be attained by simply attaching the projection unit 140 to an existing microscope. Accordingly, according to the projection unit 140 and the microscope system 2, an existing microscope system can be easily expanded to assist in a pathological diagnosis based on optical images that is performed by a pathologist.

Third Embodiment

FIG. 13 illustrates the configuration of a computer 60 included in a microscope system 3 in accordance with the present embodiment. The microscope system 3 is similar to the microscope system 1 except that the former includes the computer 60 in place of the computer 20.

The computer 60 controls the entirety of the microscope system 3. As with the computer 20, the computer 60 is connected to the microscope 100, the microscope controller 10, the display apparatus 30, the input apparatus 40, and the identification apparatus 50.

The computer 60 includes a camera control section 61, a projection image generation section 63, an information acquisition section 64, a projection control section 65, an image recording section 66, an image compositing section 67, and a display control section 68 as components pertaining primarily to the controlling of the projection apparatus 133.

The camera control section 61, the information acquisition section 64, the projection control section 65, the image recording section 66, the image compositing section 67, and the display control section 68 respectively correspond to the camera control section 21, the information acquisition section 24, the projection control section 25, the image recording section 26, the image compositing section 27, and the display control section 28 included in the computer 20.

The computer 60 is very different from the computer 20 in that the former does not include a component corresponding to the image analysis section 22. The computer 60 is also different from the computer 20 in that the projection image generation section 63 performs different processes from the projection image generation section 23.

The projection image generation section 63 generates projection image data on the basis of a diagnosis protocol selected from a plurality of diagnosis protocols. Note that a diagnosis protocol refers to a series of rules, including a determination standard or a procedure extending from start to end of a diagnosis. A projection image represented by projection image data corresponds to a selected diagnosis protocol. A projection image generated by the projection image generation section 63 is output to the projection control section 65, the image recording section 66, and the image compositing section 67.

The projection image generation section 63 uses a method of selecting a diagnosis protocol that is similar to the method used by the image analysis section 22 in the microscope system 1 to select an analysis process. In particular, the projection image generation section 63 may select a diagnosis protocol on the basis of an input operation performed by the user or identification information acquired by the identification apparatus 50.

A projection image desirably includes guidance for a diagnostic procedure based on a selected diagnosis protocol. The projection image generation section 23 may determine a color for the guidance for the diagnostic procedure in accordance with the selected diagnosis protocol. Thus, the pathologist can refer to the diagnostic procedure without taking the eye from the eyepiece 104, thereby advancing the diagnosis efficiently without incorrectly taking the diagnostic procedure.

A projection image may include a reference image indicating a determination standard based on a selected diagnosis protocol. Thus, the pathologist can check an optical image and the reference image concurrently, so that the time required for the diagnosis can be reduced and the diagnostic accuracy can be improved.

In accordance with a selected diagnosis process, the projection image generation section 63 may determine a positional relationship between a projection image and an optical image to be attained on an image plane or determine whether at least a portion of the projection image is to be projected onto an outside of the optical image.

When the setting of the microscope system 3 does not satisfy a requirement pertaining to a selected diagnosis protocol, the projection image generation section 63 may generate projection image data such that a projection image includes an alert indication. In this way, the pathologist can make various judgments in a diagnosis under proper environment, so that the diagnostic accuracy can be improved.

The projection control section 65 may control the projection apparatus 133 in accordance with the setting of the microscope system 3. Specifically, the projection control section 65 may determine in accordance with the setting of the microscope system 3 whether to project a projection image onto the image plane, or may control the projection apparatus 133 such that the projection apparatus 133 projects a projection image onto the image plane when the microscope system 3 is in a predetermined setting. Thus, in accordance with the setting, the microscope system 3 can make a change as to whether to project a projection image onto the image plane.

Some diagnosis protocols include a procedure for measuring the area or position of a structure such as a cancer cell or the distance between structures. In this case, the projection image generation section 63 may generate projection image data including a measurement result obtained using a length measurement function of the microscope. The projection control section 65 may project a projection image including the measurement result onto the image plane.

Figure 14:
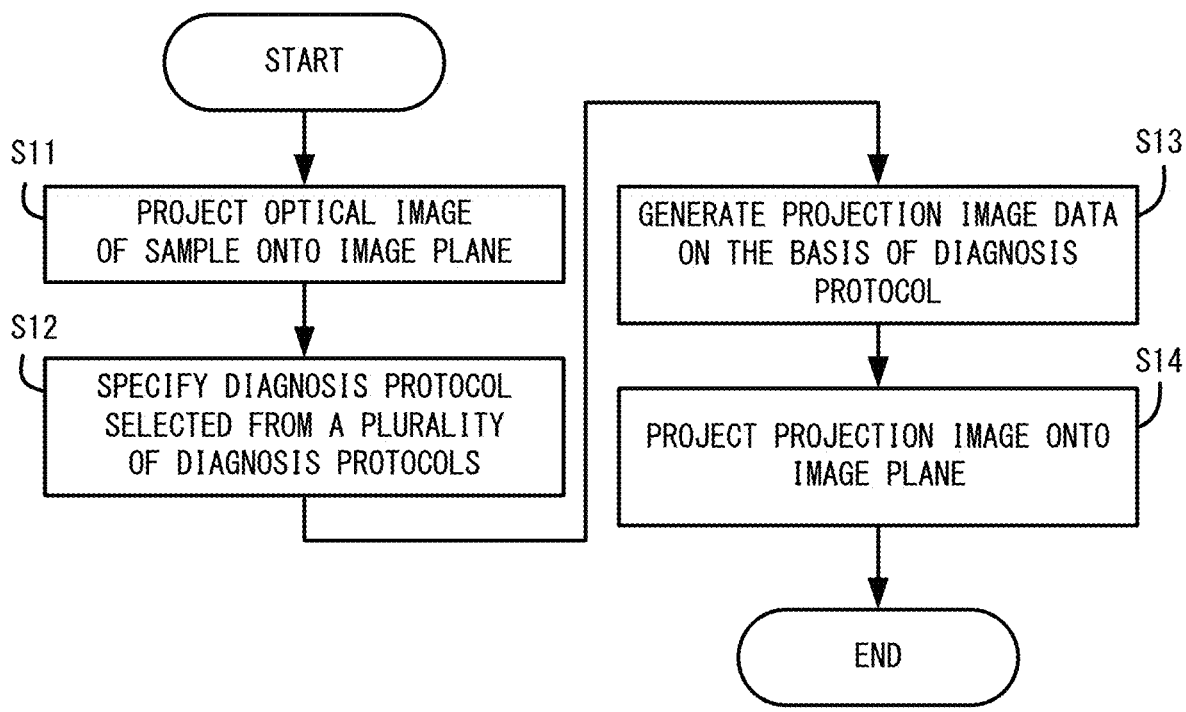
FIG. 14 is a flowchart of an image projection process performed by a microscope system 3.

The microscope system 3 configured as described above performs an image projection process depicted in FIG. 14. FIG. 14 is a flowchart of an image projection process performed by the microscope system 3. The following describes an image projection method implemented by the microscope system 3 by referring to FIG. 14.

First, the microscope system 3 projects an optical image of a sample onto an image plane (step S11). This process is similar to step S1 depicted in FIG. 3.

Next, the microscope system 3 specifies a diagnosis protocol selected from a plurality of diagnosis protocols prepared in advance (step S12). In this example, the user may select a diagnosis protocol on a selection screen, and the projection image generation section 63 may specify the selected diagnosis protocol on the basis of the input operation performed by the user.

Upon a diagnosis protocol being specified, the microscope system 3 generates projection image data on the basis of the specified diagnosis protocol (step S13). In this example, the projection image generation section 63 generates projection image data representing a projection image corresponding to the diagnosis protocol specified in step S12.

Finally, the microscope system 3 projects the projection image onto the image plane (step S14). The projection control section 65 controls the projection apparatus 133 on the basis of the projection image data, thereby causing the projection apparatus 133 to project the projection image onto the image plane. Thus, the projection image is superimposed onto the optical image of the sample.

The microscope system 3 is such that a projection image corresponding to a diagnosis protocol is displayed on an optical image. Thus, during a pathological diagnosis based on an optical image of a sample, the pathologist can obtain various information for assisting in the diagnosis, such as diagnostic procedures or determination standards, without taking the eye from the eyepiece. Meanwhile, the projection image generation section 63 generates projection image data corresponding to a diagnosis protocol selected from a plurality of diagnosis protocols, so that the microscope system 3 can deal with various types of diagnosis protocols. Hence, the microscope system 3 can assist in a pathological diagnosis based on optical images and reduce the task burden on the pathologist.

Furthermore, the microscope system 3 is similar to the microscope system 1 in that this system can reduce the burden on the pathologist with substantial rise in device cost avoided and that unlike in WSI systems, diagnosis tasks can be immediately started since no advance preparations are necessary.

FIGS. 15-18 exemplify images each viewed through the eyepiece 104 in the microscope system 3. By referring to FIGS. 15-18, the following specifically describes how an observation is performed using the microscope system 3 executing the image projection process depicted in FIG. 14. The following descriptions are given by referring to an example of a diagnosis protocol for determining whether overexpression of HER2 protein has occurred through IHC staining (hereinafter, "IHC-HER2 diagnosis protocol").

Figure 15:
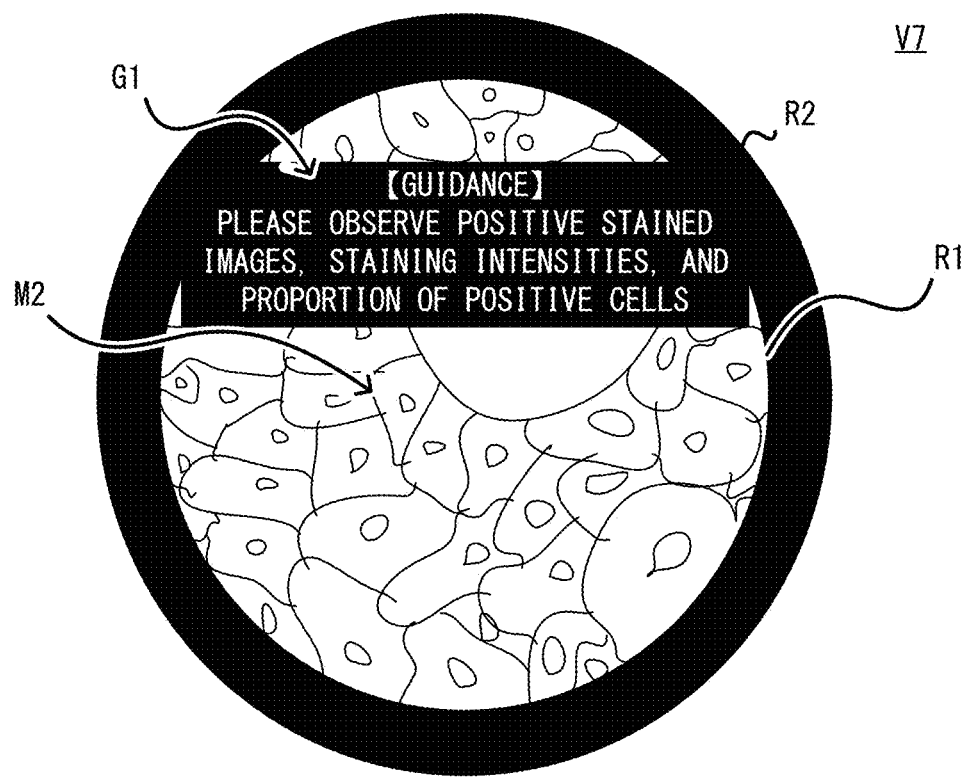
FIG. 15 illustrates an example of an image viewed through an eyepiece 104 in a microscope system 3.
Figure 16:
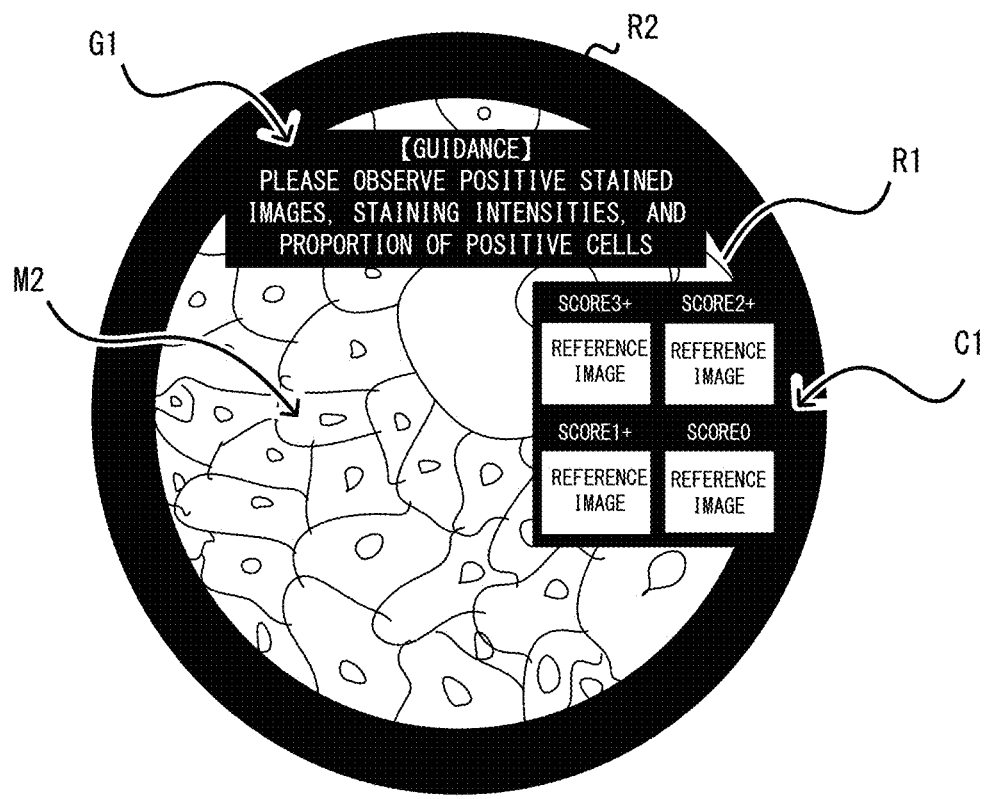
FIG. 16 illustrates another example of an image viewed through an eyepiece 104 in a microscope system 3.
Figure 17:
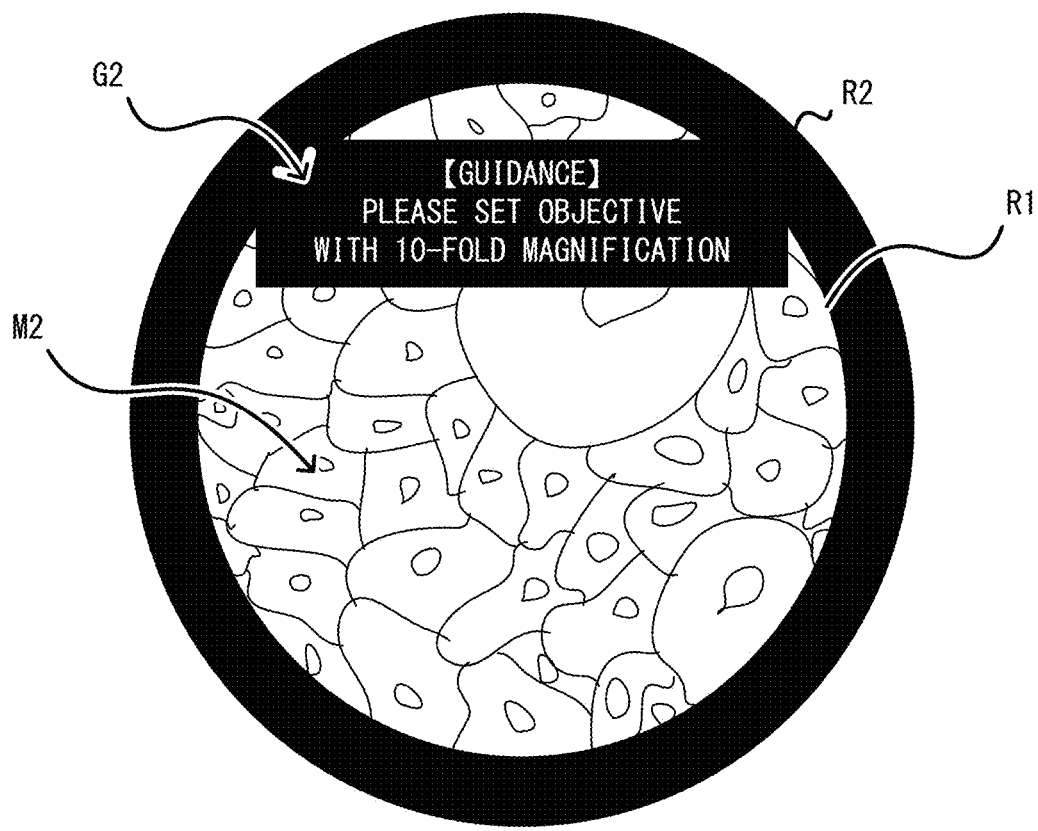
FIG. 17 illustrates still another example of an image viewed through an eyepiece 104 in a microscope system 3.
Figure 18:
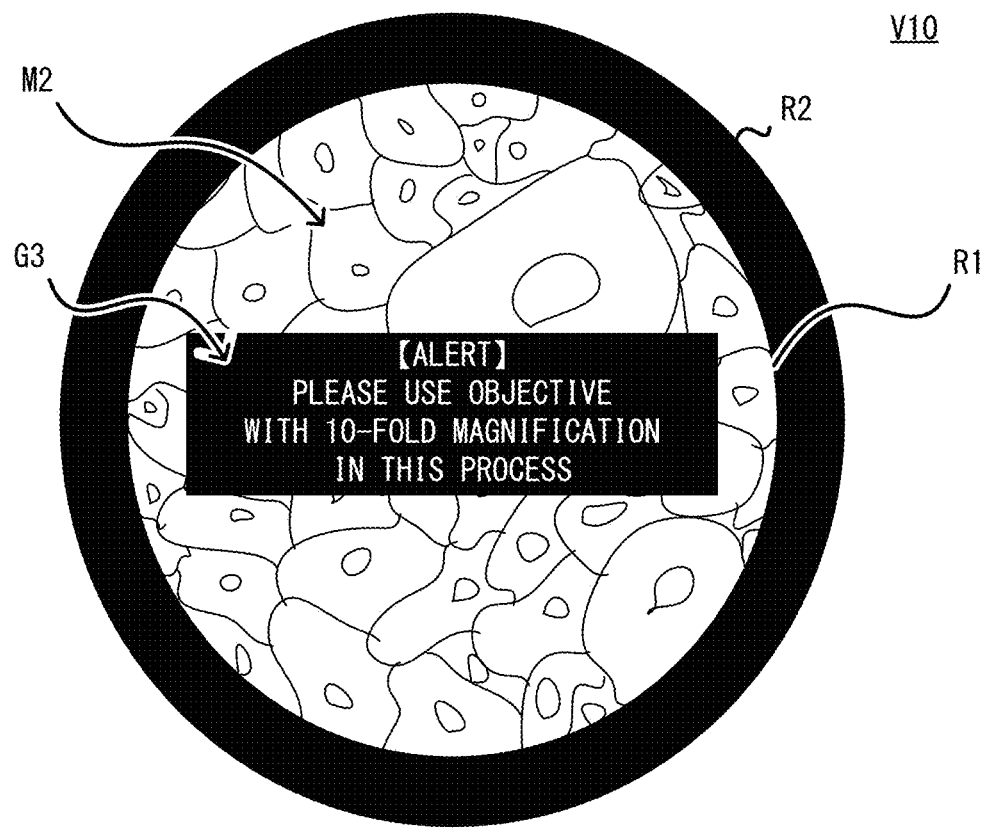
FIG. 18 illustrates yet another example of an image viewed through an eyepiece 104 in a microscope system 3.

After an observation using the microscope system 3 is started, the pathologist can observe an image V7 depicted in FIG. 15 by looking through the eyepiece 104. The image V7 is obtained by superimposing a projection image including a guidance image G1 onto an optical image M2. For example, the optical image M2 may be an image obtained using the objective 102 having a 4-fold magnification in which stained cell membranes of cancer cells are seen. The guidance image G1 provides guidance on a diagnostic procedure based on the IHC-HER2 diagnosis protocol. The IHC-HER2 diagnosis protocol establishes a procedure for observing stained images of positive HER2 protein, staining intensities, and the proportion of positive cells by using an objective having a 4-fold magnification. The guidance image G1 provides guidance on this procedure.

The microscope system 3 may have an image V8, not the image V7, projected onto the image plane. The image V8 is obtained by superimposing a projection image including the guidance image G1 and a comparative image C1 onto the optical image M2. The comparative image C1 includes a plurality of reference images indicating determination standards based on the IHC-HER2 diagnosis protocol. More specifically, the comparative image C1 includes four reference images exemplifying images that should be determined as having score 0, score 1+, score 2+, and score 3+. The pathologist can refer to the comparative image C1 when determining the proportion of positive cells.

Then, an image V9 is projected onto the image plane. The image V9 is obtained by superimposing a projection image including a guidance image G2 onto the optical image M2. The guidance image G2 provides guidance on a diagnostic procedure based on the IHC-HER2 diagnosis protocol. The IHC-HER2 diagnosis protocol specifies that an observation using an objective having a 4-fold magnification should be performed and then an observation using an objective having a 10-fold magnification should be performed. The guidance image G2 provides guidance on this procedure.

An image V10 will be projected onto the image plane when switching from the objective 102 having a 4-fold magnification to the objective 102*a* having a 10-fold magnification is not detected after projection of the image V9. The image V10 is obtained by superimposing a projection image including a guidance image G3 onto the optical image M2. The guidance image G3 is an alert indication for alerting the pathologist of the fact that the diagnosis has not been being performed in accordance with the diagnosis protocol. Since the pathologist can realize the error in the procedure owing to the alert indication, the microscope system 3 allows the diagnosis to be prevented from being continued using an incorrect procedure.

Fourth Embodiment

FIG. 19 illustrates the configuration of a diagnosis assistance system that includes a microscope system 4 and external browsing systems 300 in accordance with the present embodiment. The microscope system 4 is different from the microscope system 1 in that the former includes a computer 70 in place of the computer 20.

The microscope system 4 is connected to one or more external browsing systems 300 over the Internet 400. The external browsing systems 300 each include: a computer 310 provided with at least a communication control section 311; an input apparatus 320; and a display apparatus 330.

The Internet 400 is an example of a communication network. For example, the microscope system 3 and the external browsing systems 300 may be connected via a virtual private network (VPN) or an exclusive line.

The computer 70 is different from the computer 20 in that the former includes a communication control section 29. The communication control section 29 communicates data with the external browsing systems 300.

For example, the communication control section 29 may transmit image data to the external browsing systems 300. Image data transmitted by the communication control section 29 may be, for example, composite image data generated by the image compositing section 27. Digital image data and projection image data may be individually transmitted. Alternatively, only digital image data may be transmitted. The external browsing system 300 is such that upon receipt of image data, the computer 310 displays an image on the display apparatus 330 on the basis of the image data. For example, the computer 310 may generate composite image data on the basis of digital image data and projection image data and may display a composite image on the display apparatus 330 on the basis of the composite image data.

For example, the communication control section 29 may receive operation information input by the user of the external browsing system 300. The image analysis section 22 may select an analysis process on the basis of the operation information received by the communication control section 29. Using the projection apparatus 133, the microscope system 4 may project a projection image based on an input operation performed by the user of the external browsing system 300 onto the image plane.

The microscope system 4 can communicate with the external browsing systems 300 connected thereto over the network. Hence, the pathological diagnosis can be performed while the users at different locations are communicating with each other.

The embodiments described above indicate specific examples to facilitate understanding of the invention, and the present invention is not limited to these embodiments. Various modifications or changes can be made to the microscope system, the projection unit, and the image projection method without departing from the recitation in the claims.

FIG. 12 exemplifies the projection unit 140 including the image analysis section 142 that performs an analysis process selected from a plurality of analysis processes. However, the projection unit may include a projection image generation section that generates projection image data on the basis of a diagnosis protocol selected from a plurality of diagnosis protocols.

FIG. 19 exemplifies the microscope system 4, which corresponds to the microscope system 1 with the function for communicating with the external browsing systems 300 added thereto. However, the function for communicating with the external browsing systems 300 may be added to the microscope system 2 so as to form a new microscope system.

FIG. 1 indicates an example in which the projection image generation section 23 generates projection image data on the basis of a selected analysis process and an analysis result from the analysis process. However, the projection image generation section 23 may generate first projection image data on the basis of a selected analysis process and an analysis result from the analysis process and generate second projection image data on the basis of a selected diagnosis protocol. Then, the projection apparatus 133 may project a first projection image represented by the first projection image data and a second projection image represented by the second projection image data onto an optical image.

Although FIGS. 5-10 indicate examples of pathological diagnoses for breast cancer, the microscope system 1 may be used for a pathological diagnosis for other cancers such as cervical cancer. For example, when the microscope system 1 is applied to a pathological diagnosis for cervical cancer, a classification may be made on the basis of the Bethesda system, and classification results such as NILM, LSIL, HSIL, SCC, or ASC may be displayed using a projection image. In a genome diagnosis, the number of tumor cells, the total number of cells, and the ratio therebetween may be displayed using a projection image.

Examples have been indicated in which the display format of a projection image is changed according to an analysis process. However, the microscope system 1 may change the display format according to a change in the setting of the illumination optical system or the observation optical system.

Examples have been indicated in which the computer 20 in the microscope system 1 includes the image analysis section 22. However, the image analysis section 22 may be implemented by the computer 20 in the microscope system 1 and a remote module outside the microscope system 1. For example, the remote module may be a server provided on a cloud. The computer 20 may download a latest program from the remote module so as to update an analysis program, so that a new analysis process can be dealt with. Alternatively, the computer 20 may download a latest program from the remote module, so that a new diagnosis protocol can be dealt with.

Figure 20:
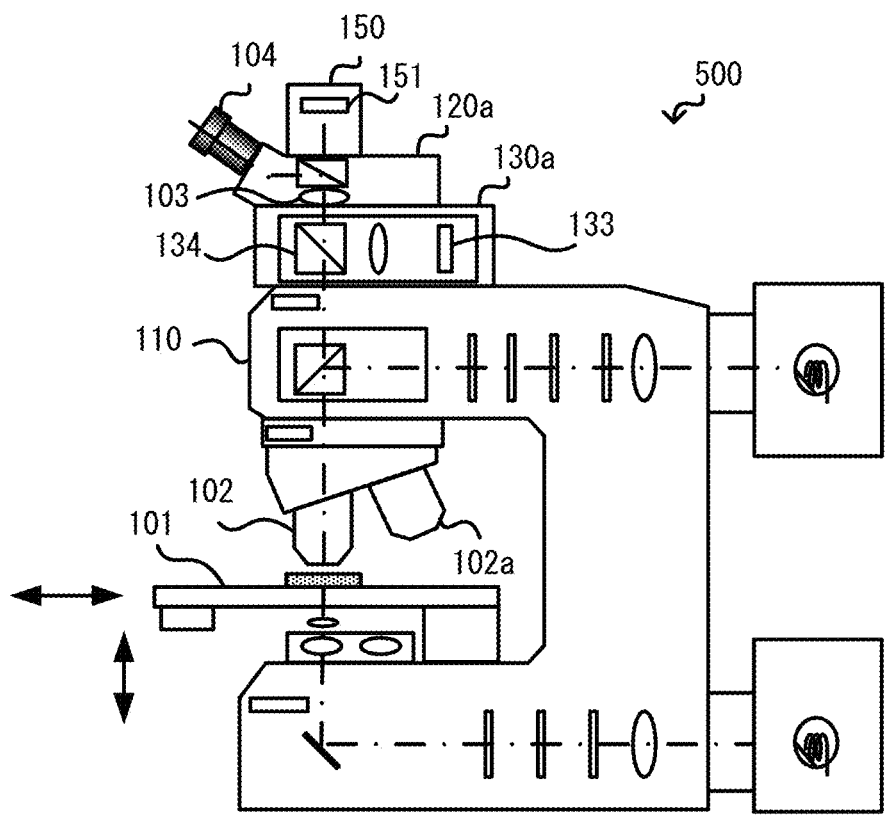
FIG. 20 illustrates the configuration of a microscope 500.

For example, the microscope system 1 may include a microscope 500 depicted in FIG. 20. The above embodiments have been described by referring to the exemplary configuration in which the intermediate tube 130 includes the image sensor 131. However, as depicted in FIG. 20, a digital camera 150 attached to a trinocular-tube 120a may be provided with an image sensor 151 for acquiring digital image data to be used for image analysis. In this case, however, light emitted from the projection apparatus 133 included in an intermediate tube 130a will be incident on the image sensor 151. Thus, the digital camera 150 may be controlled such that the light emission period of the projection apparatus 133 and the exposure period of the image sensor 151 have no overlap therebetween. In this way, a projection image can be prevented from being seen on a digital image.

A microscope system that includes the microscope 500 may be used for a diagnosis of moving objects, such as sperm sorting performed in artificial insemination or the like. In a sperm sorting, the quality of sperms is determined in accordance with information such as a sperm shape that can be determined on the basis of a still image (hereinafter, "shape information") and information such as the straightness and speed of sperm movement that can be determined on the basis of a moving image or a plurality of still images (hereinafter, "movement information"). Thus, an analysis process for assisting in a sperm sorting task may include outputting movement information of sperms to be reflected in a projection image and may further include specifying candidates for sperms to be selected by the user by using shape information and movement information of sperms.

More specifically, first, upon the user starting to observe sperms to be subjected to selection, the image analysis section 22 calculates paths of sperm movements by analyzing a plurality of pieces of digital image data acquired at different times. Then, the projection image generation section 23 generates projection image data on the basis of the analysis result, and the projection apparatus 133 projects a projection image including path indications MT onto the image plane. The path indications MT each indicate a movement path that a sperm has taken to reach the current position. The path indications MT may each indicate a movement path for a period from a predetermined time before the present time (e.g., three seconds before the present time) up to the present time.

Accordingly, the user can first observe an image V11 depicted in FIG. 21 that includes an optical image M3 and, upon the image analysis section 22 finishing an analysis process, observe an image V12 depicted in FIG. 21 that includes an optical image M4 and an assistance image A1. The assistance image A1 includes the path indications MT of individual sperms so that the user observing the image V12 can determine, at a glance, characteristics of the shapes of the sperms as well as characteristics of movements thereof. Hence, the determination of the quality of sperms performed by the user can be facilitated, thereby reducing the burden of selection task.

In addition, the image analysis section 22 analyzes digital image data of a superimposition image obtained by superimposing the assistance image A1 onto the optical image M4 so as to specify candidates for sperms to be selected by the user. Then, the projection image generation section 23 generates projection image data on the basis of an analysis result including position information of the specified sperms, and the projection apparatus 133 projects a projection image including region-of-interest indications ROI onto the image plane. The region-of-interest indications ROI are intended to encourage the user to give attention to the sperms specified by the image analysis section 22 and may be, for example, rectangular or circular graphic patterns surrounding the sperms. Alternatively, the region-of-interest indications ROI may display the probabilities of sperms being of good quality by using differences between the colors of the graphic patterns.

Accordingly, the user can observe an image V13 depicted in FIG. 21 that includes the optical image M4 and an assistance image A2. The assistance image A2 includes the region-of-interest indications ROI in addition to the path indications MT. Thus, the user can determine, at a glance, characteristics of the shapes of sperms as well as characteristics of movements thereof, as in the case of the image V12. Furthermore, the user can prioritize observation of the sperms specified by the region-of-interest indications ROI so that sperms of good quality can be early selected. Hence, the burden of selection task is further reduced.

Figure 22:
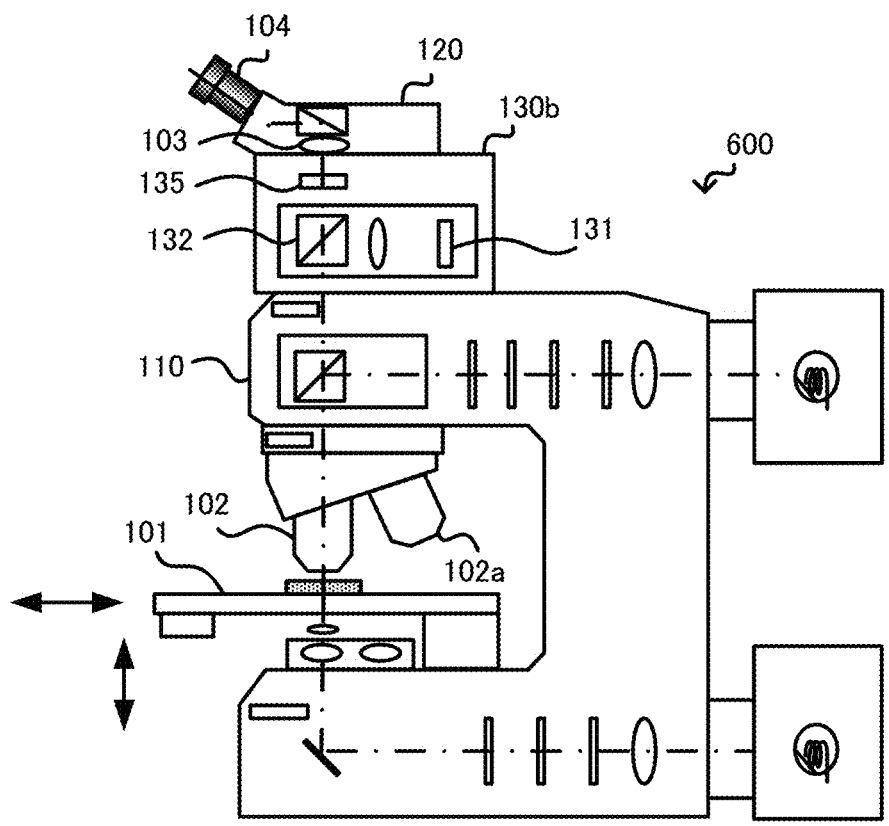
FIG. 22 illustrates the configuration of a microscope 600.

For example, the microscope system 1 may include a microscope 600 depicted in FIG. 22. The microscope 600 is provided with an intermediate tube 130b that includes a projection apparatus 135 using a transmissive liquid crystal device, instead of the intermediate tube 130. The above embodiments have been described by referring to the exemplary configuration in which a projection image is projected onto the image plane by deflecting light emitted from the projection apparatus 133 by means of the light deflection element 134 disposed on the light path between the objective 102 and the eyepiece 104. However, as depicted in FIG. 22, the projection apparatus 135 may be disposed on the light path between the objective 102 and the eyepiece 104.

The above embodiments have been described by referring to the example in which an image sensor is included as the photodetector. However, the photodetector is not limited to an image sensor. For example, the above-described technique may be provided for a scanning microscope, and in this case, the photodetector may be a photomultiplier tube (PMT).

In addition, the described microscope system may adjust the brightness of at least either an optical image or a projection image in accordance with a selected analysis process or may adjust the brightness of at least either an optical image or a projection image in accordance with a selected diagnosis protocol. The brightness may be adjusted by controlling the light quantity of a light source or by controlling the quantity of transmitted light by using a variable ND filter.

The above embodiments have been described by exemplifying a keyboard, a mouse, a joystick, a touch panel, and the like as the input apparatus 40. However, the input apparatus 40 may be an apparatus that receives voice input, e.g., a microphone. In this case, the computer 20 may have a function for recognizing a voice instruction input from the input apparatus 40, and for example, the information acquisition section 24 included in the computer 20 may convert voice data into operation information by using a voice recognition technique and output the result to the projection image generation section 23.

What is claimed is:

1. A microscope system comprising:
   an eyepiece;
   an objective that guides light from a stained sample to the eyepiece;
   a tube lens that is disposed on a light path between the eyepiece and the objective and that forms an optical image of the sample based on light therefrom;
   a projection apparatus that projects a projection image onto an image plane on which the optical image is formed; and
   a processor configured to perform processes comprising:
   (1) performing, for digital image data of the sample, at least one analysis process selected from a plurality of analysis processes, the analysis processes using a plurality of trained neural networks and being intended for a plurality of different staining methods or cancer types used for pathological diagnoses, and the at least one analysis process including classifying, into at least one class from among one or more classes, at least one structure seen in a digital image represented by the digital image data, and generating position information specifying a position of the structure classified into the at least one class;
(2) outputting an analysis result of the at least one analysis process, the analysis result including the position information; and
(3) generating projection image data based on the analysis result and the staining method or the cancer type for which the at least one analysis process is intended, wherein:
the projection image represented by the projection image data is an image that includes a position image consisting of a graphic pattern and that represents the analysis result in a display format that corresponds to the at least one analysis process, the graphic pattern indicating the position of the structure classified into the at least one class and having a color or form different for each class into which the classification was performed,
the color of the projection image or the form for the graphic pattern constituting the projection image are determined based on the staining method or the cancer type for which the at least one analysis process is intended,
the display format includes a color of an image or a form for the graphic pattern of the image, and
the structure classified into the at least one class is an object that serves as a basis for a judgment to be made by a pathologist in a pathological diagnosis.

2. The microscope system of claim 1, wherein:
the display format further includes an image position, and
the generating the projection image data includes determining, in accordance with the at least one analysis process, a positional relationship between the projection image and the optical image to be attained on the image plane.

3. The microscope system of claim 2, wherein the generating the projection image data includes determining, in accordance with the at least one analysis process, whether at least a portion of the projection image is to be projected onto an outside of the optical image.

4. The microscope system of claim 1, wherein the microscope system adjusts a brightness of at least one of the optical image and the projection image in accordance with the at least one analysis process.

5. The microscope system of claim 1, wherein:
the performing the at least one analysis process includes generating statistical information of the structure classified into the at least one class,
the analysis result includes the statistical information, and
the projection image further includes the statistical information.

6. The microscope system of claim 1, wherein the processor is configured to perform further processes comprising:
determining, in accordance with a setting of the microscope system, whether to project the projection image onto the image plane, and
controlling the projection apparatus such that the projection apparatus projects the projection image onto the image plane when the microscope system is in a predetermined setting.

7. The microscope system of claim 1, wherein the performing the at least one analysis process includes selecting the at least one analysis process based on an input operation performed by a user.

8. The microscope system of claim 1, further comprising:
an identification apparatus that obtains identification information assigned to the sample,
wherein the performing the at least one analysis process includes selecting the at least one analysis process based on the identification information obtained by the identification apparatus.

9. The microscope system of claim 1, further comprising:
an input apparatus that outputs an operation signal corresponding to an input operation performed by a user,
wherein the performing the at least one analysis process includes changing some of thresholds to be used in the at least one analysis process in accordance with the operation signal output from the input apparatus.

10. The microscope system of claim 1, wherein:
the at least one analysis process includes a classification process of classifying, into at least one class, at least one cell present in the digital image represented by the digital image data based on a staining intensity,
the analysis result includes class information into which the at least one cell has been classified, and the position information specifies outlines of the at least one cell or nuclei thereof, and
the position image represents, by a color different for each class of the at least one cell classified by the classification process as indicated by the class information, a position of the least one cell specified by the position information.

11. The microscope system according to claim 10, wherein:
the at least one analysis process includes a statistical process of generating statistical information for each class of the at least one cell classified by the classification process,
the analysis result includes the statistical information, and
the projection image includes the position image and a statistical image representing the statistical information.

12. The microscope system of claim 1, wherein:
the plurality of analysis processes are intended for a plurality of different combinations of staining methods used for a pathological diagnosis and biomarkers used for the pathological diagnosis, and
the processor is configured to perform processes comprising:
generating the projection image data based on a combination of the analysis result and a stained portion in a cell stained in accordance with the staining method and biomarker for which the at least one analysis process is intended,
generating the position image such that insides of cell nuclei are painted over when the stained portion is nuclei of cells, and
generating the position image such that cell outlines are clarified when the stained portion is cell membranes.

13. The microscope system of claim 1, wherein:
the processor determines, as the color of the projection image, a color different from a color of an optical image, and
the color of the optical image is based on the staining method for which the at least one analysis process is intended.

14. The microscope system of claim 1, further comprising:
a storage that records the digital image data and the projection image data, the projection image data being stored in the storage in association with the digital image data in an area different from an area in which the digital image data is stored.

15. The microscope system of claim 1, wherein the processor is further configured to perform a process of downloading a parameter of a new neural network, and adding an analysis process that is performed by using the new neural network to the plurality of analysis processes.

16. A projection unit for a microscope provided with an objective, a tube lens, and an eyepiece, the projection unit comprising:
- an imaging apparatus that acquires digital image data of a stained sample based on light therefrom;
- a projection apparatus that projects a projection image onto an image plane on which an optical image of the sample is formed by the tube lens; and
- a processor configured to perform processes comprising:
  - (1) performing, for digital image data of the sample, at least one analysis process selected from a plurality of analysis processes, the analysis processes using a plurality of trained neural networks and being intended for a plurality of different staining methods or cancer types used for pathological diagnoses, and the at least one analysis process including classifying, into at least one class from among one or more classes, at least one structure seen in a digital image represented by the digital image data, and generating position information specifying a position of the structure classified into the at least one class;
  - (2) outputting an analysis result of the at least one analysis process, the analysis result including the position information; and
  - (3) generating projection image data based on the analysis result and the staining method or the cancer type for which the at least one analysis process is intended, wherein:
- the projection image represented by the projection image data is an image that includes a position image consisting of a graphic pattern and that represents the analysis result in a display format that corresponds to the at least one analysis process, the graphic pattern indicating the position of the structure classified into the at least one class and having a color or form different for each class into which the classification was performed,
- the color of the projection image or the form for the graphic pattern constituting the projection image are determined based on the staining method or the cancer type for which the at least one analysis process is intended,
- the display format includes a color of an image or a form for the graphic pattern of the image, and
- the structure classified into the at least one class is an object that serves as a basis for a judgment to be made by a pathologist in a pathological diagnosis.

* * * * *